US007722880B2

(12) United States Patent
McBride et al.

(10) Patent No.: US 7,722,880 B2
(45) Date of Patent: May 25, 2010

(54) **IMMUNOREACTIVE 38-KDA FERRIC BINDING PROTEIN OF *EHRLICHIA CANIS* AND USES THEREOF**

(75) Inventors: Jere W. McBride, League City, TX (US); David H. Walker, Galveston, TX (US); Christopher Kuyler Doyle, Bacliff, TX (US)

(73) Assignee: Research Development Foundation, Carson City, NV (US)

( * ) Notice: Subject to any disclaimer, the term of this patent is extended or adjusted under 35 U.S.C. 154(b) by 478 days.

(21) Appl. No.: 11/066,648

(22) Filed: Feb. 25, 2005

(65) Prior Publication Data

US 2005/0260621 A1 Nov. 24, 2005

Related U.S. Application Data

(60) Provisional application No. 60/547,499, filed on Feb. 25, 2004.

(51) Int. Cl.
| | |
|---|---|
| *A61K 39/00* | (2006.01) |
| *A61K 39/02* | (2006.01) |
| *A61K 39/38* | (2006.01) |
| *A61K 45/00* | (2006.01) |
| *C12P 21/08* | (2006.01) |

(52) U.S. Cl. .............. 424/190.1; 424/184.1; 424/185.1; 424/234.1; 424/278.1; 424/400; 424/404; 530/388.4; 530/389.5; 930/10; 930/200

(58) Field of Classification Search ................ 424/9.34, 424/184.1, 185.1, 190.1, 234.1, 278.1; 435/69.3; 530/300, 350; 536/23.7; 930/10, 200, 290
See application file for complete search history.

(56) References Cited

OTHER PUBLICATIONS

Yu et al. 1999. J. Clin. Microbio. vol. 37(8): 2568-2575.*
GenBank accession No. AF117273. Erlichia chaffeensis surface protein precursor and iron-binding protein. Nov. 1, 1999.*
An Immunoreactive 37-kDa Protein of Ehrlichia canis Shares Structural Homology and Iron-Binding Capacity with the Ferric Binding Protein Family. presentation. Abstract and powerpoint. C. Kuyler Doyle, Xiaofeng Zhang, David H. Walker, and Jere W. McBride.*
Yu et al., (J. of Clin. Microbio. 1999. vol. 37(8): 2568-2575).*
Adhikari et al., "Biochemical characterization of a *Haemophilus influenzae* periplasmic iron transport operon," *J. Biol. Chem.*, 270: 25142-25149, 1995.
Adhikari et al., "The fbpABC locus of *Neisseria gonorrhoeae* functions in the periplasm-to-cytosol transport of iron," *J. Bacteriol.*, 178: 2145-2149, 1996.
Andrews et al., "Bacterial iron homeostasis," *Fems Microbiol. Rev.*, 27: 215-237, 2003.
Angerer et al., "Nucleotide sequences of the sfuA, sfuB, and sfuC genes of *Serratia marcescens* suggest a periplasmic-binding-protein-dependent iron transport mechanism," *J. Bacteriol.*, 172: 572-578, 1990.

Ashrafian, "Hepcidin: the Missing Link between Hemochromatosis and Infections," *Infection and Immunity*, 71(12): 6693-6700, 2003.
Barnewall et al., "*Ehrlichia chaffeensis* and *E. seenetsu* , but Not the Human Granulogytic Ehrlichiosis Agent, Colocalize with Transferrin Receptor and Up-Regulate Transferrin Receptor mRNA by Activating Iron-Responsive Protein 1," *Infection and Immunity*, 67(5):2258-2265, 1999.
Bearden et al., "An ABC transporter system of *Yersinia pestis* allows utilization of chelated iron by *Escherichia coli* SAB11," *J. Bacteriol.*, 180: 1135-1147, 1998.
Bearden et al., "The Yfe system of *Yersinia pestis* transports iron and manganese and is required for full virulence of plague," *Mol. Microbiol.*, 32:403-414, 1999.
Bonnah et al., "Alteration of epithelial cell transferrin-iron homeostasis by *Neisseria meningitidis* and *Neisseria gonorrhoeae,*" *Cellular Microbiology*, 2(3): 207-218, 2000.
Clarke et al., "Structural biology of bacterial iron uptake systems," *Curr. Top. Med. Chem.*, 1:7-30, 2001.
Desai et al., "Analysis of Fur binding to operator sequences within the *Neisseria gonorrhoeae* fbpA promoter," *J. Bacteriol.*, 178: 5020-5023, 1996.
Doyle et al., "An Immunoreactive 37-kDa Protein of *Ehrlichia canis* Shares Structural Homology and Iron-Binding Capacity with the Ferric Binding Protein Family," presentation (abstract and power point).
Doyle et al., "An Immunoreactive 38-Kilodalton Protein of *Ehrlichia canis* Shares Structural Homology and Iron-Binding Capacity with the Ferric Ion-Binding Protein Family," *Infection and Immunity*, 73(1): 62-69, 2005.
Janakiraman et al., "The putative iron transport system SitABCD encoded on SPI1 is required for full virulence of *Salmonella typhimurium,"* Mol. Microbiol.*, 35: 1146-1155, 2000.
Kirby et al., "The *Pasteurella haemolytica* 35 kDa iron-regulated protein is an FbpA homologue," *Microbiology*, 144(Pt 12): 3425-3436, 1998.
Larson et al., "Replication of *Neisseria meningitidis* within Epithelial Cells Requires TonB-Dependent Acquisition of Host Cell Iron," *Infection and Immunity*, 70(3): 1461-1467, 2002.
McBride et al., "Immunodiagnosis of *Ehrlichia canis* Infection with Recombinant Proteins," *J. Clin. Microbiology*, 39(1): 315-322, 2001.
Paddock et al., "*Ehrlichia chaffeensis*: a Prototypical Emerging Pathogen," *Clin. Microb. Rev.*, 16(1): 37-64, 2003.
Yu et al., "Comparison of *Ehrlichia chaffeensis* recombinant proteins for serologic diagnosis of human monocytotropic ehrlichiosis," *J. Clin. Microbiol.*, 37: 2568-2575, 1999.
Zhu et al., "Oxo-iron clusters in a bacterial iron-trafficking protein: new roles for a conserved motif," *Biochem. J.*, 376: 35-41, 2003.

(Continued)

*Primary Examiner*—Mark Navarro
*Assistant Examiner*—JaNa Hines
(74) *Attorney, Agent, or Firm*—Fulbright & Jaworski, L.L.P.

(57) ABSTRACT

The present invention is directed to the cloning, sequencing, expression, and characterization of an immunoreactive ferric binding protein (Fbp) (38-kDa) protein of *Ehrlichia canis* encoded by a polynucleotide therefor. In particular embodiments, the protein is employed in an immunogenic composition, such as a vaccine. Methods to induce an immune reaction in an individual with compositions of the invention are provided.

6 Claims, 7 Drawing Sheets

OTHER PUBLICATIONS

Barnewall et al., "*Ehrlichia chaffeensis* inclusions are early endosomes which selectively accumulate transferrin receptor," *Infection and Immunity*, 65(4): 1455-1461, 1997.

Database NCBI Online, "conserved hypothetical protein [Thermotoga maritima MSB8]", AAD35554, Online <http://www.ncbi.nlm.nih.gov/entrez/viewer.fcgi?db=protein&id=4980978>.

"Lalign output for Yu vs. Seq ID No. 2" <http://www.ch.embnet.org/cgi-bin/LALIGN form parser>, Dec. 1, 2007, Europe/Zurich.

Merriam-Webster Online Dictionary; Definition of "About", <http://www.merriam-webster.com/dictionary/about>.

"Summary of the 18$^{th}$ meeting Rocky Gap Lodge & Golf Resort, Cumberland, Maryland, Sep. 28-Oct. 1, 2003", American Society for Rickettsiology; ASR Newsletter Archives, Oct. 2003, Online <http://www.cas.umt.edu/rickettsiology/new

FIG. 4

IMMUNOREACTIVE 38-KDA FERRIC BINDING PROTEIN OF *EHRLICHIA CANIS* AND USES THEREOF

CROSS-REFERENCE TO RELATED APPLICATIONS

The present invention claims priority to U.S. Provisional Patent Application Ser. No. 60/547,499, filed Feb. 25, 2004, which is incorporated by reference herein in its entirety.

FIELD OF THE INVENTION

The present invention relates generally to the fields of cellular biology, molecular biology, pathology, clinical microbiology, and medicine. Specifically, the present invention concerns the molecular biology of *Ehrlichia*, including *Ehrlichia canis*. More specifically, the present invention relates to molecular cloning and characterization of a 38-kDa immunoreactive ferric binding protein (Fbp) polynucleotide and the encoded product from *Ehrlichia canis*, as well as uses thereof.

BACKGROUND OF THE INVENTION

*Ehrlichia* spp. are obligately intracellular gram-negative bacteria that reside in endosomes within hematopoietic cells and infect various hosts including humans, domestic and wild canidae, deer, horses, sheep, cattle, and wild rodents. Each member of the family Anaplasmataceae has its own particular primary target cell tropism. Most species of *Ehrlichia* are either monocytotropic (e.g. *E. canis*, *E. chaffeensis*, and *E. muris*) or granulocytotropic (e.g. *Anaplasma phagocytophilum*, and *E. ewingii*) with the exceptions of *Ehrlichia ruminantium*, which grows in the endothelial cells of the host, *Anaplasma marginale*, a red blood cell parasite, and *Anaplasma platys*, a platelet parasite.

Although *Ehrlichiae* were described in the early part of the 20$^{th}$ century, they received very little attention because they were considered pathogens of only veterinary importance in the United States until the recent two decades. The renewed interest in *Ehrlichia* is due to the emergence of ehrlichioses affecting humans. Since 1987, three emerging human ehrlichial pathogens (*E. chaffeensis*, *E. ewingii*, and *A. phagocytophilum*) have been discovered in the United States.

*Ehrlichia canis*, the prototype species of the genus, is the etiologic agent of canine monocytotropic ehrlichiosis (CME). CME, also known as canine tropical pancytopenia, is a worldwide disease transmitted by the brown dog tick, *Rhipicephalus sanguineus*. The progression of canine ehrlichiosis occurs in three phases: acute, sub-clinical and chronic. The acute phase is characterized by fever, anorexia, depression, lymphadenopathy and mild thrombocytopenia. Dogs typically recover from the acute phase, but become persistently infected carriers of the organism without clinical signs of disease for months or even years. A chronic phase develops in some cases that is characterized by thrombocytopenia, hyperglobulinemia, anorexia, emaciation, and hemorrhage, particularly epistaxis, followed by death. Each year it costs millions of dollars worldwide for treating companion and working dogs infected with *E. canis*. *Ehrlichia canis* was isolated from a human recently, and thus may be an emerging public health threat.

One aspect of *E. canis* biology concerns the need for iron, which is a necessity for survival of nearly all prokaryotes and eukaryotes. For the obligate intracellular bacterium *Ehrlichia chaffeensis*, the importance of iron for intracellular survival has been demonstrated by inhibition of *Ehrlichia* proliferation in the presence of the intracytoplasmic iron chelator deferoxamine (Barnewall et al., 1997). Early endosomes containing the bacteria (morulae) upregulate and accumulate the mammalian transferrin receptor (Barnewall et al., 1997), suggesting that the organism has developed specific strategies for iron acquisition. The cytoplasmic vacuole where the *Ehrlichia* resides is acidic, which may promote the release of free iron into the compartment (Barnewall et al., 1997). An *E. chaffeensis* protein with homology to known ferric binding proteins has been previously reported (Yu et al., 1999), but the mechanisms of iron acquisition by *Ehrlichia* spp. are unknown and functional demonstration of iron binding properties of *Ehrlichia* Fbps has not been experimentally demonstrated. Furthermore, the *E. chaffeensis* Fbp polypeptide is not immunoreactive.

Iron is involved in many key metabolic functions of the cell, but insoluble $Fe(OH)_3$ (rust) forms at a physiological pH and thus must be stored and transferred via iron binding proteins (Andrews et al., 2003; Mietzner et al., 1998). In eukaryotic systems, extracellular iron-binding proteins include transferrin and lactoferrin, while ferritin binds and sequesters intracellular iron. Protein-bound iron also inhibits the interaction of Fe(II) with $O_2$, preventing the formation of free radicals that are damaging to cells (Andrews et al., 2003; Mietzner et al., 1998). The availability of iron has been demonstrated to increase the virulence of many diverse pathogenic bacteria (Raymond et al., 2003). Limiting the availability of free iron is a mechanism to naturally suppress growth of bacteria. However, under the selective pressure of the limited iron available in the host, pathogenic bacteria have evolved specific iron acquisition mechanisms including iron binding molecules and proteins.

Bacteria commonly utilize siderophores as means of iron mobilization. These molecules are nonproteinaceous iron chelators that are expressed, secreted, and bound by surface receptors that enable the transport of free iron from the environment (Andrews et al., 2003; Mietzner et al., 1998). Another means of iron uptake involves iron acquisition from the host iron binding proteins transferrin and lactoferrin (Andrews et al., 2003; Mietzner et al., 1998). This mechanism, used by many gram-negative pathogens involves a conserved system by which iron is competed away from transferrin or lactoferrin at the outer membrane of the bacterium and the iron is shuttled across the membrane and into the periplasm (Andrews et al., 2003). Mobilization of iron into the cytoplasm involves three proteins that belong to the ATP-binding cassette (ABC) transporter family, the ferric binding protein (Fbp), a cytoplasmic permease, and an ATP-binding protein (Adhikari et al., 1996; Adhikari et al., 1995; Andrews et al., 2003; Clarke et al., 2001; Mietzner et al., 1998), all encoded by an operon system that is shared among many diverse bacterial species including *Neisseria gonorrhoeae, Haemophilus influenzae, Mannheimia (Pasteurella) haemolytica, Serratia marcescens, Salmonella typhimurium*, and *Yersinia pestis* (Adhikari et al., 1996; Adhikari et al., 1995 Angerer et al., 1990; Bearden and Perry, 1999; Bearden et al., 1998; Janakiraman and Slauch, 2000; Kirby et al., 1998). The operon system of *Neisseria gonorrhoeae* has been demonstrated to be under the control of the iron regulatory element Fur (ferric uptake regulator)(Desai et al., 1996).

Identifying the genetic and antigenic compositions of *E. canis* is essential for studying the pathogenesis of canine ehrlichiosis and developing an effective vaccine. Although Yu et al. (1999) describe an *E. chaffeensis* 37-kDa protein that is homologous to the iron (III)-binding periplasmic protein precursor of gram-negative bacteria, the prior art is deficient in the cloning and characterization of immunoreactive gene of *Ehrlichia canis*. The present invention fulfills this long-standing need and desire in the art by cloning an immunoreactive Fbp of *Ehrlichia canis*.

BRIEF SUMMARY OF THE INVENTION

The present invention describes the molecular cloning, sequencing, expression, and characterization of a 38-kDa immunoreactive ferric binding protein gene of *Ehrlichia canis*.

In particular, the present invention represents the first functional characterization of a ferric binding protein (Fbp) ortholog in any obligate intracellular bacteria. The present inventors have identified an immunoreactive 38-kDa Fbp from *Ehrlichia canis* that shares homology with a known family of periplasmic Fbps involved in iron acquisition in extracellular bacterium. Structural modeling of the *E. canis* Fbp identified an iron-binding motif conserved among the Fbp family, and the present inventors demonstrated the ability of *E. canis* Fbp to bind free iron. *E. canis* Fbp was observed primarily in the cytoplasm of bacteria with reticulate morphology, while surface and extracellular distribution on morula fibers and the membrane of morulae was observed on the dense-cored *Ehrlichial* form. Notably, *E. canis* fbp was not organized with other prototypical iron acquisition genes in an operon system.

The exemplary *E. canis* Fbp protein sequence provided herein had homology (~25-60%) with a known family of ferric binding proteins (Fbp), indicating that it plays a role in iron acquisition known to be essential for *Ehrlichia* survival, in specific embodiments of the invention. The predicted three-dimensional structure of *E. canis* Fbp demonstrated conservation of Fbp structural motifs. In the presence of iron, the recombinant Fbp exhibited visible absorbance spectrum compared to the unbound form, indicative of iron binding.

The gene encoding the orthologous Fbp from *E. chaffeensis*, the closely related causative agent of human disease, exhibits 87% homology to the Fbp protein of *E. canis*. A recombinant *E. canis* Fbp fusion protein reacted with antibodies in sera from dogs with canine ehrlichiosis, and antisera produced against recombinant *E. canis* Fbp recognized a native protein of similar molecular mass (38-kDa) from *E. canis* whole cell lysates. In particular embodiments of the invention, these studies demonstrate that Fbp is a highly conserved iron binding protein that is important for its survival and also is a viable target for vaccine use.

In one embodiment of the present invention, there is DNA sequence encoding a 38-kDa immunoreactive Fbp of *Ehrlichia canis*. In particular embodiments, the protein has an amino acid sequence of SEQ ID NO:2 and the gene has a nucleic acid sequence of SEQ ID NO:1. In specific embodiments of the invention, the *E. canis* Fbp polypeptide comprises one or more of the following characteristics: 1) it is immunoreactive; 2) it binds iron, such as Fe(III), although in alternative embodiments it binds Fe(II) instead or in addition to; 3) it comprises an N-terminal sequence, which may be referred to as a signal sequence, and which may be cleaved after post-translational modification resulting in the production of a mature protein (predicted to be about 35.8-kDa); 4) it comprises a tyrosine at positions 201, 202, or both; 5) it comprises a lysine at position 14; 5) it comprises a tyrosine at 145 and/or an arginine at positions 13, 105, and 139; 6) it may be cytoplasmically localized and/or localized on the surface and extracellular morula fibers; and 7) it comprises two domains each comprised of a central β-sheet surrounded by multiple α-helices, which are thereby connected with a hinge of antiparallel β-strands. In specific embodiments, the polypeptide is isolated and/or purified.

In specific embodiments of the present invention, there is the polypeptide of SEQ ID NO:2 or a related *E. canis* Fbp polypeptide. As used herein, the term "related *E. canis* Fbp polypeptide" refers to a polypeptide having similar sequence with SEQ ID NO:2, such as described below, and the related polypeptide is not necessarily naturally present in *E. canis* but may be derived from SEQ ID NO:2 and/or may be generated synthetically. In specific embodiments, mutations to SEQ ID NO:2, either by mutating an amino acid or by mutating a polynucleotide that encodes SEQ ID NO:2, are encompassed in the invention. Such mutations may be produced either chemically or by site-directed mutagenesis, for example. In specific embodiments, the related *E. canis* Fbp polypeptide comprises one or more of the same characteristics as native SEQ ID NO:2, including immunoreactivity and iron-binding capability, for example.

The *E. canis* Fbp of the present invention may comprise sequence identity with the polypeptide of SEQ ID NO:2. For example, a polypeptide of the invention may be about 70% identical to SEQ ID NO:2, about 75% identical to SEQ ID NO:2, about 80% identical to SEQ ID NO:2, about 85% identical to SEQ ID NO:2, about 90% identical to SEQ ID NO:2, about 95% identical to SEQ ID NO:2, about 97% identical to SEQ ID NO:2, about 99% identical to SEQ ID NO:2, and so forth. In other embodiments, an Fbp polypeptide of the invention comprises at least about 325 contiguous amino acids from SEQ ID NO:2, at least about 300 contiguous amino acids from SEQ ID NO:2, at least about 250 contiguous amino acids from SEQ ID NO:2, at least about 200 contiguous amino acids from SEQ ID NO:2, at least about 150 contiguous amino acids from SEQ ID NO:2, at least about 125 contiguous amino acids from SEQ ID NO:2, at least about 100 contiguous amino acids from SEQ ID NO:2, at least about 75 contiguous amino acids from SEQ ID NO:2, at least about 50 contiguous amino acids from SEQ ID NO:2, or at least about 25 contiguous amino acids from SEQ ID NO:2, for example.

Polynucleotides that encode SEQ ID NO:2, such as the exemplary SEQ ID NO:1 polynucleotide, or that encode related proteins as discussed above, are embodiments of the invention and may comprise one or more of the following characteristics: 1) it comprises an iron-regulatory element, such as the exemplary ferric uptake regulator (Fur)-binding site; an exemplary *E. coli* Fur recognition consensus, for example, comprises ATA/TAT; 2) it encodes a polypeptide comprising one or more of the *E. canis* Fbp polypeptide characteristics described herein; and 3) it is not comprised on an operon.

In particular embodiments of the invention, there is a polynucleotide that comprises sequence identity with SEQ ID NO:1. For example, a polynucleotide of the invention may be about 70% identical to SEQ ID NO:1, about 75% identical to SEQ ID NO:1, about 80% identical to SEQ ID NO:1, about 85% identical to SEQ ID NO:1, about 90% identical to SEQ ID NO:1, about 95% identical to SEQ ID NO:1, and so forth. In other embodiments, an Fbp polynucleotide of the invention comprises at least about 1000 contiguous nucleotides from SEQ ID NO:1, at least about 750 contiguous nucleotides from SEQ ID NO:1, at least about 500 contiguous nucleotides from SEQ ID NO:1, at least about 300 contiguous nucleotides from SEQ ID NO:1, at least about 250 contiguous nucleotides from SEQ ID NO:1, at least about 200 contiguous nucleotides from SEQ ID NO:1, at least about 150 contiguous nucleotides from SEQ ID NO:1, at least about 100 contiguous nucleotides from SEQ ID NO:1, SEQ ID NO:1, at least about 75 contiguous nucleotides from SEQ ID NO:1, at least about 50 contiguous nucleotides from SEQ ID NO:1, at least about 25 contiguous nucleotides from SEQ ID NO:1, or at least about 12 contiguous nucleotides from SEQ ID NO:1.

In specific aspects of the invention, there is an isolated polynucleotide that specifically hybridizes under highly stringent conditions to the complement of the sequence set forth in SEQ ID NO:1.

In another embodiment of the present invention, there is provided an expression vector comprising a polynucleotide of the invention encoding a 38-kDa immunoreactive Fbp of *E. canis*, and the vector is capable of expressing the polynucleotide, such as when the vector is introduced into a cell. The cell into which the vector is introduced may be a prokaryotic cell or it may be a eukaryotic cell, and any elements comprised on the vector, such as regulatory elements, are capable of expressing the Fbp polynucleotide therein. Exemplary regulatory elements include iron-binding elements, promoters, enhancers, origin of replication, and so forth, for example.

In still another embodiment of the present invention, there is provided a recombinant protein comprising an amino acid sequence of SEQ ID NO:2. In specific embodiments, the amino acid sequence is encoded by a nucleic acid sequence of SEQ ID NO:1. The recombinant protein may be useful as an antigen. In specific embodiments, the polypeptide of SEQ ID NO:2 or a related *E. canis* Fbp polypeptide is employed as an immunogen, and in specific embodiments it induces an immune response in an individual to which the polypeptide is delivered. In specific embodiments, the polypeptide induces an immune response such that it provides immunity to subsequent challenge, such as from *E. canis* infection.

Immunogenic compositions of the present invention may comprise an immunoreactive polypeptide of SEQ ID NO:2 or a related *E. canis* Fbp polypeptide; it may comprise antibodies to a polypeptide of SEQ ID NO:2 or a related *E. canis* Fbp polypeptide; or it may comprise both. The present invention provides a considerable advantage for *E. canis* protection over *E. chaffeensis* protection, wherein the orthologous Fbp polypeptide of *E. chaffeensis* is not immunoreactive and it has not been demonstrated to bind iron. Thus, in specific embodiments of the invention, there is a vaccine comprising SEQ ID NO:2 or a related *E. canis* Fbp polypeptide. In particular aspects of the invention, the vaccine is a subunit vaccine and does not comprise the *E. canis* organism as a whole.

In particular aspects of the invention, the *E. canis* Fbp polypeptide of the invention is immunoreactive. That is, in specific embodiments the polypeptide binds to, which may be referred to as reacts with, an antibody, such as the antibodies in the serum of an individual, for example. One of skill in the art recognizes that there are multiple ways to demonstrate immunoreactivity, such as, for example, by providing a recombinant protein suspected of being immunoreactive, introducing the protein into an animal, such as a rabbit or dog, collecting the antiserum, and then determining if antibodies in the antisera recognize the recombinant protein, such as on a western blot. In another exemplary embodiment, serum from an *E. canis*-infected animal, such as a dog, is probed to a blot comprising a protein suspected of being immunoreactive to determine if there is binding therebetween. Detection of binding indicates that the protein suspected of being immunoreactive is in fact immunoreactive. Lymphoproliferative responses to an antigen may be employed. Immunoreactivity assays may employ ELISA or cytometric beads, for example.

In particular embodiments, immunogenic compositions of the present invention comprise the native conformation of the polypeptide, as opposed to a denatured form, thereby preserving a conformation which comprises an epitope. In particular embodiments, the conformational epitope is an epitope that comprises a particular three-dimensional structure on the outside of the protein, for example part or all of an alpha helix, a beta sheet, a beta strand, a hinge region, two or more antiparallel beta strands, part or all of an iron-binding domain, or a combination thereof. In specific embodiments, a conformational epitope comprises tyrosine 201, tyrosine 202, tyrosine 145, arginine 13, arginine 105, arginine 139, or a combination thereof. A skilled artisan recognizes that there is software available to determine which residues of a folded polypeptide are located on the outside.

In a preferred embodiment of the present invention, there is provided a method of producing the polypeptide, comprising the steps of obtaining a vector that comprises an expression construct comprising a sequence encoding the amino acid sequence of SEQ ID NO:2 or a related polypeptide operatively linked to a promoter; transfecting the vector into a cell; and culturing the cell under suitable conditions effective for expression of the polypeptide. The polypeptide may be further defined as recombinant.

The invention may also be described in certain embodiments as a method of inhibiting *Ehrlichia canis* infection in a subject comprising the steps of: identifying a subject prior to exposure or suspected of being exposed. to or suspected of being infected with *Ehrlichia canis*; and administering a composition comprising a Fbp of *Ehrlichia canis* in an amount effective to inhibit *Ehrlichia canis* infection. The inhibition may occur through any means such as e.g., the stimulation of the subject's humoral or cellular immune responses, or by other means such as inhibiting the normal function of the Fbp, or even competing with the antigen for interaction with some agent in the subject's body, for example.

In still yet another embodiment of the present invention, there is provided a method of targeting therapy to an individual, comprising the step of administering a compound to an individual, wherein the compound has a targeting moiety and a therapeutic moiety, wherein the targeting moiety is specific for Fbp.

In an embodiment of the present invention, there is an isolated DNA sequence encoding an *Ehrlichia canis* Fbp, wherein said protein is immunoreactive with anti-*Ehrlichia canis* serum, and wherein said 38-kilodalton Fbp has amino acid sequence of SEQ ID NO:2. In particular embodiments, the DNA comprises the sequence of SEQ ID NO:1. In specific embodiments, the protein comprises an N-terminal signal sequence, an iron-binding motif, or both. The iron binding motif of the protein comprises multiple amino acids suitable for iron co-ordination including two tyrosine residues, in particular aspects of the invention. In specific embodiments, the tyrosine residues in the iron binding motif are at positions 201 and 202 of the mature protein.

In another aspect of the invention, there is a vector comprising a DNA sequence of the present invention, such as, for example, one comprising SEQ ID NO:1. In particular aspects of the invention, the vector is an expression vector capable of expressing a peptide or polypeptide comprising SEQ ID NO:1 when said expression vector is introduced into a cell. In other aspects of the invention, there is a host cell comprising a vector of the present invention, such as one comprising SEQ ID NO:1, for example.

In particular embodiments, there is a recombinant protein having the amino acid sequence of SEQ ID NO:2. In specific aspects of the invention, the amino acid sequence is encoded by a nucleic acid segment comprising sequence of SEQ ID NO:1. The recombinant protein of the invention may be comprised, such as formulated, in a pharmaceutically acceptable carrier, in some embodiments. Further embodiments include an antibody immunoreactive with a recombinant protein of the invention.

In another embodiment of the invention, there is a method of producing the recombinant protein of the invention, comprising the steps of obtaining a vector that comprises an expression construct comprising sequence encoding the amino acid sequence of SEQ ID NO:2 operatively linked to a promoter; transfecting said vector into a cell; and culturing the cell under conditions effective for expression of the sequence encoding the amino acid sequence of SEQ ID NO:2.

In an additional embodiment of the invention, there is a method of inhibiting *Ehrlichia canis* infection in an individual comprising the steps of identifying a subject prior to exposure or suspected of being exposed to or infected with *Ehrlichia canis*; and administering a composition comprising a 38-kDa *Ehrlichia canis* Fbp in an amount effective to inhibit *Ehrlichia canis* infection. In particular aspects of the invention, the Fbp is a recombinant protein comprising an amino acid sequence of SEQ ID NO:2, for example. The recombinant protein is encoded by a gene comprising of sequence of SEQ ID NO:1, in particular aspects of the invention. The composition comprising a 38-kDa antigen may be dispersed in a pharmaceutically acceptable carrier, for example.

In an additional embodiment of the present invention, there is a method of targeted therapy to an individual, comprising the step of administering a composition to an individual, wherein the composition has a therapeutic moiety and a targeting moiety specific for 38-kDa *Ehrlichia canis* Fbp protein. In specific embodiments, the targeting moiety is selected from the group consisting of an antibody specific for 38-kDa *Ehrlichia canis* Fbp and a ligand or ligand binding domain that binds 38-kDa *Ehrlichia canis* Fbp. In additional specific embodiments, the therapeutic moiety is selected from the group consisting of a radioisotope, a toxin, a chemotherapeutic agent, an immune stimulant and a cytotoxic agent.

Other and further aspects, features, and advantages of the present invention will be apparent from the following description of the presently preferred embodiments of the invention given for the purpose of disclosure.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 4 shows genomic organization of *E. canis* and *E. chaffeensis* iron acquisition genes compared to the operon systems of *Neisseria gonorrhoeae* and *Yersinia pestis*, and the related rickettsial organism *Anaplasma marginale*. (Abbreviations: FbpA—ferric binding protein; MP—membrane permease; ORF—open reading frame; ATP-bp—ATP binding protein.)

DETAILED DESCRIPTION OF THE INVENTION

I. Definitions

Figure 1:
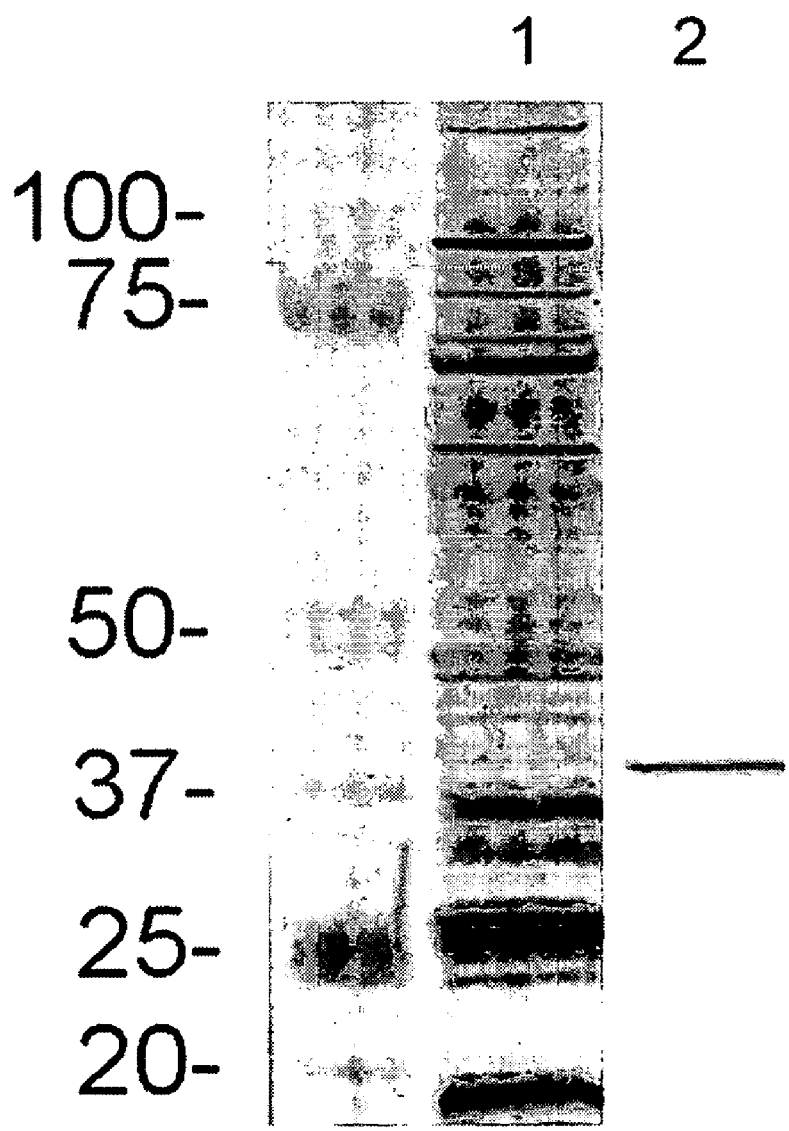
FIG. 1 depicts a western immunoblot of *E. canis* whole cell lysate probed with serum from an *E. canis* infected dog (lane 1) and monospecific rabbit anti-*E. canis* recombinant Fbp (lane 2).

As used herein the specification, "a" or "an" may mean one or more. As used herein in the claim(s), when used in conjunction with the word "comprising", the words "a" or "an"

may mean one or more than one. As used herein "another" may mean at least a second or more.

The term "conformational epitope" as used herein refers to an epitope that comprises amino acids that are not necessarily arranged sequentially but comprise a three-dimensional structure on the outside of a native folded polypeptide recognized by the antibody. That is, when a protein molecule folds into a three dimensional structure, the amino acids forming the epitope are juxtaposed such that the antibody recognizes the sequence.

The term "immunogenic" as used herein refers to a composition that is able to provoke an immune response against it.

The term "immune response" as used herein refers to the reaction of the immune system to the presence of an antigen by making antibodies to the antigen. In further specific embodiments, immunity to the antigen may be developed on a cellular level, by the body as a whole, hypersensitivity to the antigen may be developed, and/or tolerance may be developed, such as from subsequent challenge. In specific embodiments, an immune response entails lymphocytes identifying an antigenic molecule as foreign and inducing the formation of antibodies and lymphocytes capable of reacting with it and rendering it less harmful.

The term "immunoreactive" as used herein refers to a composition being reactive with antibodies from the sera of an individual. In specific embodiments, a composition is immunoreactive if an antibody recognizes it, such as by binding to it.

The term "subunit vaccine" as used herein refers to a vaccine wherein a polypeptide or fragment thereof is employed, as opposed to an entire organism.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1983]; "Transcription and Translation" [B. D. Hames & S. J. Higgins eds. (1984)1; "Animal Cell Culture" [R. I. Freshney, ed. (1986)1; "Immobilized Cells And Enzymes" [IRL Press, (1986)1; B. Perbal, "A Practical Guide To Molecular Cloning" (1984).

II. The Present Invention

The present invention concerns compositions and methods related to *Ehrlichia* spp. proteins and the polynucleotides that encode them. In particular, the present invention concerns one or more ferric ion-binding proteins (Fbp) from *Ehrlichiae* spp, which may be referred to as FbpA, in specific embodiments. In further embodiments, the present invention relates to a Fbp from *Ehrlichia* spp. that is about 38-kDa. In additional embodiments, the 38 kDa fbp is from *E. canis.*

In particular aspects, the present invention is drawn to the discovery of a functional ferric binding protein (p38) in *Ehrlichia canis*, which represents the first protein described with ferric binding capacity associated with obligate intracellular bacteria. The identification of ferric binding proteins in *Ehrlichiae* represents a target for intervention and furthermore provides the first step in understanding the mechanisms of iron acquisition by the organism—as well as other obligate intracellular bacteria.

The *E. canis* Fbp protein sequence shared homology (~25-60%) with a known family of ferric binding proteins (Fbp), suggesting it may play a role in iron acquisition known to be essential for *Ehrlichia* survival. The gene encoding the orthologous ferric binding protein from *E. chaffeensis* exhibits 87% homology with *E. canis* Fbp. The amino acid sequence of iron binding motif of *E. canis* Fbp comprises two tyrosine residues, which are important components of the iron binding potential of the Fbp family as well as other reported key residues. In addition, *E. canis* Fbp three-dimensional structure demonstrated conservation of characteristic Fbp family structural motifs—two domains liked with a polypeptide "hinge" region. Under iron-binding conditions, the recombinant Fbp exhibited intense red color and visible absorbance spectrum in the 400-500 nm range, indicative of iron binding activity.

In addition, the present invention also demonstrates that the *E. canis* Fbp does not remain in the periplasmic space as do other bacterial ferric binding proteins, but can be found in the cytoplasm and on the surface as well, in particular embodiments. The *E. canis* Fbp protein contained a signal sequence suggesting that the Fbp protein could be transported to the periplasm, outer membrane, or extracellularly, thereby shuttling free iron into the bacteria for utilization. Furthermore, this invention also demonstrated that the serum from experimentally infected dogs recognized *E. canis* Fbp recombinant protein in a conformationally dependent manner, thereby confirming its immunogenicity.

Some embodiments of the present invention are directed toward a method of inhibiting *Ehrlichia canis* infection in a subject comprising the steps of: identifying a subject prior to exposure or suspected of being exposed to or infected with *Ehrlichia canis*; and administering a composition comprising a 38-kDa antigen of *Ehrlichia canis* in an amount effective to inhibit *Ehrlichia canis* infection. The inhibition may occur through any means such as e.g., the stimulation of the subject's humoral or cellular immune responses, or by other means such as inhibiting the normal function of the 38-kDa antigen, or even competing with the antigen for interaction with some agent in the subject's body, or a combination thereof, for example.

The present invention is also directed toward a method of targeted therapy to an individual, comprising the step of administering a compound to an individual, wherein the compound has a targeting moiety and a therapeutic moiety, and wherein the targeting moiety is specific for Fbp protein. Preferably, the targeting moiety is an antibody specific for Fbp or ligand or ligand binding domain that binds Fbp. Likewise, the therapeutic moiety may comprise a radioisotope, a toxin, a chemotherapeutic agent, an immune stimulant, a cytotoxic agent, or an antibiotic, for example.

III. Ferric Ion-Binding Protein (Fbp)

The present invention regards a polypeptide comprising an amino acid sequence of SEQ ID NO:2, wherein the polypeptide may be a recombinant protein or it may be isolated and/or purified from nature, for example. In particular aspects, the amino acid sequence is encoded by a nucleic acid sequence of SEQ ID NO:1. The polypeptide is useful as an antigen, in specific embodiments.

The present invention is also directed towards a method of producing the recombinant protein, comprising the steps of obtaining a vector that comprises an expression construct comprising a sequence encoding the amino acid sequence of SEQ ID NO:2 operatively linked to a promoter; transfecting the vector into a cell; and culturing the cell under conditions effective of the expression construct.

By a "substantially pure protein" is meant a protein that has been separated from at least some of those components that naturally accompany it. A substantially pure immunoreactive Fbp of *Ehrlichia canis* may be obtained, for example, by extraction from a natural source; by expression of a recombinant nucleic acid encoding an immunoreactive Fbp of *Ehrlichia canis*; or by chemically synthesizing the protein, for example. Accordingly, substantially pure proteins include prokaryotic proteins synthesized in *E. coli*, other prokaryotes, or any other organism in which they do not naturally occur.

The present invention concerns an *Ehrlichia* Fbp, and in particular embodiments relates to the polynucleotide of SEQ ID NO:1 that encodes the polypeptide of SEQ ID NO:2.

Thus, in certain embodiments, the present invention concerns novel compositions comprising at least one proteinaceous *E. canis* Fbp molecule. As used herein, a "proteinaceous molecule," "proteinaceous composition," "proteinaceous compound," "proteinaceous chain" or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues, and any range derivable therein.

As used herein, an "amino acid molecule" refers to any polypeptide, polypeptide derivative, or polypeptide mimetic as would be known to one of ordinary skill in the art. In certain embodiments, the residues of the proteinaceous molecule are sequential, without any non-amino acid molecule interrupting the sequence of amino acid molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In certain embodiments the proteinaceous composition comprises at least one protein, polypeptide or peptide. In further embodiments, the proteinaceous composition comprises a biocompatible protein, polypeptide or peptide. As used herein, the term "biocompatible" refers to a substance that produces no significant untoward effects when applied to, or administered to, a given organism according to the methods and amounts described herein. Such untoward or undesirable effects are those such as significant toxicity or adverse immunological reactions.

Proteinaceous compositions may be made by any technique known to those of skill in the art, including the expression of proteins, polypeptides or peptides through standard molecular biological techniques, the isolation of proteinaceous compounds from natural sources, or the chemical synthesis of proteinaceous materials, for example. The nucleotide and protein, polypeptide and peptide sequences for various genes have been previously disclosed, and may be found at computerized databases known to those of ordinary skill in the art. Two such databases are the National Center for Biotechnology Information's Genbank and GenPept databases, for example. The coding regions for these known genes may be amplified and/or expressed using the techniques disclosed herein or as would be know to those of ordinary skill in the art. Alternatively, various commercial preparations of proteins, polypeptides and peptides are known to those of skill in the art.

In certain embodiments a proteinaceous compound may be purified. Generally, "purified" will refer to a specific or protein, polypeptide, or peptide composition that has been subjected to fractionation to remove various other proteins, polypeptides, or peptides, and which composition substantially retains its activity, as may be assessed, for example, by the protein assays, as would be known to one of ordinary skill in the art for the specific or desired protein, polypeptide or peptide. Exemplary activities that may be assessed for retention in the purified proteinaceous composition are iron-binding activity and immunoreactivity.

In specific embodiments of the present invention, a Fbp polypeptide is labeled, and any detectable label is suitable in the invention. The label may be attached to the Fbp polypeptide at the N-terminus, at the C-terminus, or in a side chain of an amino acid residue. One or more labels may be employed. Exemplary labels included radioactive labels, fluorescent labels, colorimetric labels, and so forth. In specific embodiments, the label is covalently attached to the polypeptide.

IV. *E. canis* Fbp Nucleic Acid Compositions

Certain embodiments of the present invention concern a Fbp nucleic acid. In certain aspects, a Fbp nucleic acid comprises a wild-type or a mutant Fbp nucleic acid. In particular aspects, a Fbp nucleic acid encodes for or comprises a transcribed nucleic acid. In other aspects, a Fbp nucleic acid comprises a nucleic acid segment of SEQ ID NO:1, or a biologically functional equivalent thereof. In particular aspects, a Fbp nucleic acid encodes a protein, polypeptide, peptide.

The term "nucleic acid" is well known in the art and may be used interchangeably herein with the term "polynucleotide.". A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

A. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, carboxyalkyl, amino, hydroxyl, halogen (i.e., fluoro, chloro, bromo, or iodo), thiol or alkylthiol moeity. Preferred alkyl (e.g., alkyl, carboxyalkyl, etc.) moieties comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like.

A nucleobase may be comprised in a nucleoside or nucleotide, using any chemical or natural synthesis method described herein or known to one of ordinary skill in the art.

B. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

C. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

D. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as fluorescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moiety which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moiety replacing phosphodiester backbone moiety used for improved nuclease resistance, cellular uptake and regulating RNA expression; U.S. Pat. No. 5,858,988 which describes hydrophobic carrier agent attached to the 2'-O position of oligonucleotides to enhanced their membrane permeability and stability; U.S. Pat. No. 5,214,136 which describes oligonucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

E. Polyether and Peptide Nucleic Acids

In certain embodiments, it is contemplated that a nucleic acid comprising a derivative or analog of a nucleoside or nucleotide may be used in the methods and compositions of the invention. A non-limiting example is a "polyether nucleic acid", described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid", also known as a "PNA", "peptide-based nucleic acid analog" or "PENAM", described in U.S. Pat. Nos. 5,786,461, 5891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or. nucleosides that comprise a nucleobase moiety, a nucleobase linker moiety that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

In certain embodiments, a nucleic acid analogue such as a peptide nucleic acid may be used to inhibit nucleic acid amplification, such as in PCR, to reduce false positives and discriminate between single base mutants, as described in U.S. Pat. No. 5891,625. Other modifications and uses of nucleic acid analogs are known in the art, and are encompassed by the Fbp polynucleotide. In a non-limiting example, U.S. Pat. No. 5,786,461 describes PNAs with amino acid side chains attached to the PNA backbone to enhance solubility of the molecule. In another example, the cellular uptake property of PNAs is increased by attachment of a lipophilic group. U.S. application Ser. No. 117,363 describes several alkylamino moieties used to enhance cellular uptake of a PNA. Another example is described in U.S. Pat. Nos. 5,766,855, 5,719,262, 5,714,331 and 5,736,336, which describe PNAs comprising naturally and non-naturally occurring nucleobases and alkylamine side chains that provide improvements in sequence specificity, solubility and/or binding affinity relative to a naturally occurring nucleic acid.

F. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

G. Purification of Nucleic Acids

A nucleic acid may be purified on polyacrylamide gels, cesium chloride centrifugation gradients, or by any other means known to one of ordinary skill in the art (see for example, Sambrook et al., 1989, incorporated herein by reference).

In certain aspect, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

H. Nucleic Acid Segments

In certain embodiments, the nucleic acid is a nucleic acid segment. As used herein, the term "nucleic acid segment," are smaller fragments of a nucleic acid, such as for non-limiting example, those that encode only part of the Fbp peptide or polypeptide sequence. Thus, a "nucleic acid segment" may comprise any part of a gene sequence, of from about 2 nucleotides to the full length of the Fbp peptide or polypeptide encoding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10 mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

I. Nucleic Acid Complements

The present invention also encompasses a nucleic acid that is complementary to a Fbp nucleic acid. In specific embodiments, for example, a nucleic acid is employed for antisense or siRNA purposes, such as to inhibit at least partially expression of E. canis Fbp.

In particular embodiments the invention encompasses a nucleic acid or a nucleic acid segment complementary to the sequence set forth in SEQ ID NO:1, for example. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

J. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

V. Nucleic Acid-based Expression Systems

In particular embodiments, the present invention concerns a polynucleotide that encodes an immunoreactive E. canis Fbp, and also includes delivering the polynucleotide encoding a ferric ion-binding protein or encoded product thereof to an individual in need thereof, such as an individual infected with *Erhlichia* and/or an individual susceptible to being infected with an Fbp.

The present invention is directed toward substantially pure and/or isolated DNA sequence encoding an 38-kDa immunoreactive Fbp of *Ehrlichia canis*. In specific embodiments, the protein has an amino acid sequence of SEQ ID NO:2 and the gene has a nucleic acid sequence of SEQ ID NO:1. Generally, the encoded protein comprises an N-terminal sequence, which may be cleaved after post-translational modification resulting in the production of mature protein, which is predicted to be 35.8-kDa. Furthermore, the encoded protein comprises an iron-binding motif, which in addition to other reported key residues also comprises two tyrosine residues.

It is well known in the art that because of the degeneracy of the genetic code (i.e., for most amino acids, more than one nucleotide triplet (codon) codes for a single amino acid), different nucleotide sequences can code for a particular amino acid, or polypeptide. Thus, the polynucleotide sequences of the subject invention include SEQ ID NO. 1 or a degenerate variant of such a sequence. In particular aspects of the invention, a degenerate variant comprises a sequence that is not identical to SEQ ID NO:1 or SEQ ID NO:2 but that still retains one or more properties of SEQ ID NO:1 or SEQ ID NO:2, respectively.

As used herein, "substantially pure DNA" means DNA that is not part of a milieu in which the DNA naturally occurs, by virtue of separation (partial or total purification) of some or all of the molecules of that milieu, or by virtue of alteration of sequences that flank the claimed DNA. The term therefore includes, for example, a recombinant DNA which is incorporated into a vector, into an autonomously replicating plasmid or virus, or into the genomic DNA of a prokaryote or eukaryote; or that exists as a separate molecule (e.g., a cDNA or a genomic or cDNA fragment produced by polymerase chain reaction (PCR) or restriction endonuclease digestion) independent of other sequences. It also includes a recombinant DNA, which is part of a hybrid gene encoding additional polypeptide sequence, e.g., a fusion protein.

The present invention is further directed to an expression vector comprising a polynucleotide encoding an immunoreactive Fbp of *Ehrlichia canis* and capable of expressing the polynucleotide when the vector is introduced into a cell. In specific embodiments, the vector comprises in operable linkage the following: a) an origin of replication; b) a promoter; and c) a DNA sequence coding for the Fbp protein (SEQ ID NO. 2), for example.

As used herein "vector" may be defined as a replicable nucleic acid construct, e.g., a plasmid or viral nucleic acid. Vectors may be used to amplify and/or express nucleic acid encoding an immunoreactive Fbp (SEQ ID NO. 2) of *Ehrlichia canis*. An expression vector is a replicable construct in which a nucleic acid sequence encoding a polypeptide is operably linked to suitable control sequences capable of effecting expression of the polypeptide in a cell. The need for such control sequences will vary depending upon the cell selected and the transformation method chosen. Generally, control sequences include a transcriptional promoter and/or enhancer, suitable mRNA ribosomal binding sites, and sequences that control the termination of transcription and translation, for example. Methods that are well-known to those skilled in the art can be used to construct expression vectors comprising appropriate transcriptional and translational control signals. See for example, the techniques described in Sambrook et al., 1989, Molecular Cloning: A Laboratory Manual (2nd Ed.), Cold Spring Harbor Press, N.Y. A polynucleotide sequence to be expressed and its transcription control sequences are defined as being "operably linked" if the transcription control sequences effectively control the transcription of the polynucleotide sequence. Vectors of the invention include, but are not limited to, plasmid vectors and viral vectors. Preferred viral vectors of the invention are those derived from retroviruses, adenovirus, adeno-associated virus, SV40 virus, or herpes viruses, for example.

In general, expression vectors comprise promoter sequences that facilitate the efficient transcription of the polynucleotide to be expressed, are used in connection with a host cell. As used herein, the term "host" is meant to include not only prokaryotes but also eukaryotes, such as yeast, plant and animal cells. A recombinant polynucleotide that encodes an immunoreactive Fbp of *Ehrlichia canis* of the present invention, can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

The following description concerns exemplary elements, reagents, and methods for Fbp polynucleotides and nucleic acid delivery of an *Ehrlichia* Fbp polynucleotide.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the beta lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell, organelle, cell type, tissue, organ, or organism chosen for expression. Those of skill in the art of molecular biology generally know the use of promoters, enhancers, and cell type combinations for protein expression, (see, for example Sambrook et al., 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

5. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

9. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, E. coli is often transformed using derivatives of pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, E. coli LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with beta galactosidase, ubiquitin, and the like.

Bacterial host cells, for example, E. coli, comprising the expression vector are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

10. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may comprise a viral vector that encode one or more compositions or other components such as, for example, an immunomodulator or adjuvant. Non-limiting examples of virus vectors that may be used to deliver a nucleic acid of the present invention are described below.

a. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

b. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the compositions of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

c. Retroviral Vectors

Retroviruses have useful as delivery vectors due to their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding a composition of interest) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and that is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

d. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

e. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

11. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); by PEG mediated transformation of protoplasts (Omirulleh et al., 1993; U.S. Pat. Nos. 4,684,611 and 4,952,500, each incorporated herein by reference); by desiccation/inhibition mediated DNA uptake (Potrykus et al., 1985), and any combination of such methods. Through the application of techniques such as these, organelle(s), cell(s), tissue(s) or organism(s) may be stably or transiently transformed.

a. Ex vivo Transformation

Methods for tranfecting vascular cells and tissues removed from an organism in an ex vivo setting are known to those of skill in the art. For example, canine endothelial cells have been genetically altered by retrovial gene transfer in vitro and transplanted into a canine (Wilson et al., 1989). In another example, yucatan minipig endothelial cells were tranfected by retrovirus in vitro and transplated into an artery using a double-ballonw catheter (Nabel et al., 1989). Thus, it is contemplated that cells or tissues may be removed and tranfected ex vivo using the nucleic acids of the present invention. In particular aspects, the transplanted cells or tissues may be placed into an organism. In preferred facets, a nucleic acid is expressed in the transplated cells or tissues.

b. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection of vaccines are well known to those of ordinary skill in the art (e.g., injection of a composition comprising a saline solution). Further embodiments of the present invention include the introduction of a nucleic acid by direct microinjection. Direct microinjection has been used to introduce nucleic acid constructs into Xenopus oocytes (Harland and Weintraub, 1985). The amount of composition used may vary upon the nature of the antigen as well as the organelle, cell, tissue or organism used c. Electroporation In certain embodiments of the present invention, a nucleic acid is introduced into an organelle, a cell, a tissue or an organism via electroporation. Electroporation involves the exposure of a suspension of cells and DNA to a high voltage electric discharge. In some variants of this method, certain cell wall degrading enzymes, such as pectin degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre B lymphocytes have been transfected with human kappa immunoglobulin genes (Potter et al., 1984), and rat hepatocytes have been transfected with the chloramphenicol acetyltransferase gene (Tur Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

d. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV 1, BHK, NIH3T3 and HeLa cells were transfected with a neomycin marker gene (Chen and Okayama, 1987), and rat hepatocytes were transfected with a variety of marker genes (Rippe et al., 1990).

e. DEAE Dextran

In another embodiment, a nucleic acid is delivered into a cell using DEAE dextran followed by polyethylene glycol. In this manner, reporter plasmids were introduced into mouse myeloma and erythroleukemia cells (Gopal, 1985).

f. Sonication Loading

Additional embodiments of the present invention include the introduction of a nucleic acid by direct sonic loading. LTK fibroblasts have been transfected with the thymidine kinase gene by sonication loading (Fechheimer et al., 1987).

g. Liposome-Mediated Transfection

In a further embodiment of the invention, a Fbp nucleic acid may be comprised with a lipid complex such as, for example, comprised in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome encapsulated DNA (Kaneda et al., 1989). In other embodiments, a liposome may be complexed or employed in conjunction with nuclear non histone chromosomal proteins (HMG 1) (Kato et al., 1991). In yet further embodiments, a liposome may be complexed or employed in conjunction with both HVJ and HMG 1. In other embodiments, a delivery vehicle may comprise a ligand and a liposome.

h. Receptor-Mediated Transfection

Still further, a nucleic acid may be delivered to a target cell via receptor mediated delivery vehicles. These take advantage of the selective uptake of macromolecules by receptor-mediated endocytosis that will be occurring in a target cell. In view of the cell type specific distribution of various receptors, this delivery method adds another degree of specificity to the present invention.

Certain receptor mediated gene targeting vehicles comprise a cell receptor specific ligand and a nucleic acid binding agent. Others comprise a cell receptor specific ligand to which the nucleic acid to be delivered has been operatively attached. Several ligands have been used for receptor mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present invention, a ligand will be chosen to correspond to a receptor specifically expressed on the target cell population.

In other embodiments, a nucleic acid delivery vehicle component of a cell specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell. Such systems have been shown to be functional using systems in which, for example, epidermal growth factor (EGF) is used in the receptor mediated delivery of a nucleic acid to cells that exhibit upregulation of the EGF receptor.

In still further embodiments, the nucleic acid delivery vehicle component of a targeted delivery vehicle may be a liposome itself, which will preferably comprise one or more lipids or glycoproteins that direct cell specific binding. For example, lactosyl ceramide, a galactose terminal asialganglioside, have been incorporated into liposomes and observed an increase in the uptake of the insulin gene by hepatocytes (Nicolau et al., 1987). It is contemplated that the tissue specific transforming constructs of the present invention can be specifically delivered into a target cell in a similar manner.

i. Microprojectile Bombardment

Microprojectile bombardment techniques can be used to introduce a nucleic acid into at least one, organelle, cell, tissue or organism (U.S. Pat. No. 5,550,318; U.S. Pat. No. 5,538,880; U.S. Pat. No. 5,610,042; and PCT Application WO 94/09699; each of which is incorporated herein by reference). This method depends on the ability to accelerate DNA coated microprojectiles to a high velocity allowing them to pierce cell membranes and enter cells without killing them (Klein et al., 1987). There are a wide variety of microprojectile bombardment techniques known in the art, many of which are applicable to the invention.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et aL., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et aL., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

12. Host Cells

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs, which could then be expressed in host cells transfected with the single vector.

A tissue may comprise a host cell or cells to be transformed with a composition of the invention. The tissue may be part or separated from an organism. In certain embodiments, a tissue may comprise, but is not limited to, adipocytes, alveolar, ameloblasts, axon, basal cells, blood (e.g., lymphocytes), blood vessel, bone, bone marrow, brain, breast, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, anthers, ascite tissue, cobs, ears, flowers, husks, kernels, leaves, meristematic cells, pollen, root tips, roots, silk, stalks, and all cancers thereof.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art (see, for example, webpage http://phylogeny.arizona.edu/tree/phylogeny.html).

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expression include, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F, lambda, prototrophic, ATCC No. 273325), DH5α, JM109, and KC8, bacilli such as *Bacillus subtilis*; and other enterobacteriaceae such as *Salmonella typhimurium*, *Serratia marcescens*, various *Pseudomonas specie*, as well as a number of commercially available bacterial hosts such as SURE® Competent Cells and SOLOPACK Gold Cells (STRATAGENE®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

13. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. No. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the proteins, polypeptides or peptides produced by the methods of the invention may be "overexpressed", i.e., expressed in increased levels relative to its natural expression in cells. Such overexpression may be assessed by a variety of methods, including radio labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell and, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g. 8M) or chaotropic agents such as guanidine hydrochloride in the presence of reducing agents, such as beta mercaptoethanol or DTT (dithiothreitol), and refolded into a more desirable conformation, as would be known to one of ordinary skill in the art.

VI. Immunological Compositions

In particular embodiments of the invention, immunological compositions are employed. For example, antibodies may be utilized to bind Fbp, thereby rendering the Fbp molecule at least partially ineffective for its activity. In other embodiments, antibodies to Fbp are employed in diagnostic aspects of the invention, such as for detecting the presence of Fbp from a sample. Exemplary samples may be from an animal suspected of *E. canis* infection, from an animal susceptible to *E. canis* infection, or from an animal that has an *E. canis* infection, for example. Exemplary samples may be obtained from blood, serum, cerebrospinal fluid, urine, feces, cheek scrapings, nipple aspirate, and so forth.

Purified immunoreactive Fbp of *Ehrlichia canis* or antigenic fragments of the immunoreactive Fbp of *Ehrlichia canis* can be used to generate new antibodies or to test existing antibodies (e.g., as positive controls in a diagnostic assay) by employing standard protocols known to those skilled in the art.

As is well known in the art, immunogenicity to a particular immunogen can be enhanced by the use of non-specific stimulators of the immune response known as adjuvants. Exemplary and preferred adjuvants include complete BCG, Detox, (RIBI, Immunochem Research Inc.), ISCOMS and aluminum hydroxide adjuvant (Superphos, Biosector).

Included in this invention are polyclonal antisera generated by using the immunoreactive Fbp of *Ehrlichia canis* or a fragment of the immunoreactive Fbp of *Ehrlichia canis* as an immunogen in, e.g., rabbits. Standard protocols for monoclonal and polyclonal antibody production known to those skilled in this art are employed. The monoclonal antibodies generated by this procedure can be screened for the ability to identify recombinant *Ehrlichia canis* cDNA clones, and to distinguish them from known cDNA clones, for example.

The invention encompasses not only an intact monoclonal antibody, but also an immunologically-active antibody fragment, e.g., a Fab or (Fab)2 fragment; an engineered single chain scFv molecule; or a chimeric molecule, e.g., an antibody which contains the binding specificity of one antibody, e.g., of murine origin, and the remaining portions of another antibody, e.g., of human origin.

In one embodiment, the antibody, or fragment thereof, may be linked to a toxin or to a detectable label, e.g. a radioactive label, non-radioactive isotopic label, fluorescent label, chemiluminescent label, paramagnetic label, enzyme label or colorimetric label. Examples of suitable toxins include diphtheria toxin, Pseudomonas exotoxin A, ricin, and cholera toxin. Examples of suitable enzyme labels include malate hydrogenase, staphylococcal nuclease, delta-5-steroid isomerase, alcohol dehydrogenase, alpha glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholinesterase, etc. Examples of suitable radioisotopic labels include $^3H$, $^{125}I$, $^{131}I$, $^{32}P$, $^{35}S$, $^{14}C$, etc.

Paramagnetic isotopes for purposes of in vivo diagnosis can also be used according to the methods of this invention. There are numerous examples of elements that are useful in magnetic resonance imaging. For discussions on in vivo nuclear magnetic resonance imaging, see, for example, Schaefer et al., (1989) JACC 14, 472-480; Shreve et al., (1986) Magn. Reson. Med. 3, 336-340; Wolf, G. L., (1984) Physiol. Chem. Phys. Med. NMR 16, 93-95; Wesby et al., (1984) Physiol. Chem. Phys. Med. NMR 16, 145-155; Runge et al., (1984) Invest. Radiol. 19, 408-415. Examples of suitable fluorescent labels include a fluorescein label, an isothiocyalate label, a rhodamine label, a phycoerythrin label, a phycocyanin label, an allophycocyanin label, an opthaldehyde label, a fluorescamine label, etc. Examples of chemiluminiscent labels include a luminal label, an isoluminal label, an aromatic acridinium ester label, a luciferin label, a luciferase label, an aequorin label, etc.

Those of ordinary skill in the art will know of these and other suitable labels, which may be employed in accordance with the present invention. The binding of these labels to antibodies or fragments thereof can be accomplished using standard techniques commonly known to those of ordinary skill in the art. Typical techniques are described by Kennedy et al., (1976) Clin. Chim. Acta 70, 1-31; and Schurs et al., (1977) Clin. Chim. Acta 81, 1-40. Coupling techniques mentioned in the later are the glutaraldehyde method, the periodate method, the dimaleimide method, the maleimidobenzyl-N-hydroxy-succinimde ester method. All of these methods are incorporated by reference herein.

B. Antibodies

In certain aspects of the invention, one or more antibodies may be produced to the expressed Fbp. These antibodies may be used in various diagnostic and/or therapeutic applications described herein.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

The term "antibody" is used to refer to any antibody-like molecule that has an antigen binding region, and includes antibody fragments such as Fab', Fab, F(ab')2, single domain antibodies (DABs), Fv, scFv (single chain Fv), and the like. The techniques for preparing and using various antibody-based constructs and fragments are well known in the art. Means for preparing and characterizing antibodies are also well known in the art (See, e.g., Antibodies: A Laboratory Manual, Cold Spring Harbor Laboratory, 1988; incorporated herein by reference).

"Mini-antibodies" or "minibodies" are also contemplated for use with the present invention. Minibodies are sFv polypeptide chains which include oligomerization domains at their C-termini, separated from the sFv by a hinge region. Pack et al. (1992) Biochem 31:1579-1584. The oligomerization domain comprises self-associating .alpha.-helices, e.g., leucine zippers, that can be further stabilized by additional disulfide bonds. The oligomerization domain is designed to be compatible with vectorial folding across a membrane, a process thought to facilitate in vivo folding of the polypeptide into a functional binding protein. Generally, minibodies are produced using recombinant methods well known in the art. See, e.g., Pack et al. (1992) Biochem 31:1579-1584; Cumber et al. (1992) J Immunology 149B:120-126.

Antibody-like binding peptidomimetics are also contemplated in the present invention. Liu et al. Cell Mol Biol (Noisy-le-grand). 2003 Mar;49(2):209-16 describe "antibody like binding peptidomimetics" (ABiPs), which are peptides that act as pared-down antibodies and have certain advantages of longer serum half-life as well as less cumbersome synthesis methods.

Monoclonal antibodies (MAbs) are recognized to have certain advantages, e.g., reproducibility and large-scale production, and their use is generally preferred. The invention thus provides monoclonal antibodies of the human, murine, monkey, rat, hamster, rabbit and even chicken origin. Due to the ease of preparation and ready availability of reagents, murine monoclonal antibodies will often be preferred.

However, "humanized" antibodies are also contemplated, as are chimeric antibodies from mouse, rat, or other species, bearing human constant and/or variable region domains, bispecific antibodies, recombinant and engineered antibodies and fragments thereof. As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". A "humanized antibody" is an antibody comprising a humanized light chain and a humanized heavy chain immunoglobulin.

C. Exemplary Methods for Generating Monoclonal Antibodies

Exemplary methods for generating monoclonal antibodies (MAbs) generally begin along the same lines as those for preparing polyclonal antibodies. Briefly, a polyclonal antibody is prepared by immunizing an animal with a LEE or CEE composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. The choice of animal may be decided upon the ease of manipulation, costs or the desired amount of sera, as would be known to one of skill in the art. Antibodies of the invention can also be produced transgenically through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

As is also well known in the art, the immunogenicity of a particular immunogen composition can be enhanced by the use of non-specific stimulators of the immune response, known as adjuvants. Suitable adjuvants include all acceptable immunostimulatory compounds, such as cytokines, chemokines, cofactors, toxins, plasmodia, synthetic compositions or LEEs or CEEs encoding such adjuvants.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion is also contemplated. MHC antigens may even be used. Exemplary, often preferred adjuvants include complete Freund's adjuvant (a non-specific stimulator of the immune response containing killed Mycobacterium tuberculosis), incomplete Freund's adjuvants and aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (Smith/Kline, PA); low-dose Cyclophosphamide (CYP; 300 mg/m2) (Johnson/Mead, N.J.), cytokines such as γ-interferon, IL-2, or IL-12 or genes encoding proteins involved in immune helper functions, such as B-7.

The amount of immunogen composition used in the production of polyclonal antibodies varies upon the nature of the immunogen as well as the animal used for immunization. A variety of routes can be used to administer the immunogen including but not limited to subcutaneous, intramuscular, intradermal, intraepidermal, intravenous and intraperitoneal. The production of polyclonal antibodies may be monitored by sampling blood of the immunized animal at various points following immunization.

A second, booster dose (e.g., provided in an injection), may also be given. The process of boosting and titering is repeated until a suitable titer is achieved. When a desired level of immunogenicity is obtained, the immunized animal can be bled and the serum isolated and stored, and/or the animal can be used to generate MAbs.

For production of rabbit polyclonal antibodies, the animal can be bled through an ear vein or alternatively by cardiac puncture. The removed blood is allowed to coagulate and then centrifuged to separate serum components from whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified protein, polypeptide, peptide or domain, be it a wild-type or mutant composition. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep or frog cells is also possible. The use of rats may provide certain advantages (Goding, 1986, pp. 60 61), but mice are preferred, with the BALB/c mouse being most preferred as this is most routinely used and generally gives a higher percentage of stable fusions.

The animals are injected with antigen, generally as described above. The antigen may be mixed with adjuvant, such as Freund's complete or incomplete adjuvant. Booster administrations with the same antigen or DNA encoding the antigen would occur at approximately two-week intervals.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma producing fusion procedures preferably are non antibody producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65 66, 1986; Campbell, pp. 75 83, 1984). cites). For example, where the immunized animal is a mouse, one may use P3 X 63/Ag8, X63 Ag8.653, NS1/.Ag 4 1, Sp210 Ag14, FO, NSO/U, MPC 11, MPC11 X45 GTG 1.7 and S194/5XXO Bul; for rats, one may use R210.RCY3, Y3 Ag 1.2.3, IR983F and 4B210; and U 266, GM1500 GRG2, LICR LON HMy2 and UC729 6 are all useful in connection with human cell fusions. See Yoo et al., J Immunol Methods. 2002 Mar. 1;261(1-2):1-20, for a discussion of myeloma expression systems.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8 azaguanine resistant mouse murine myeloma SP2/0 non producer cell line.

Methods for generating hybrids of antibody producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al., (1977). The use of electrically induced fusion methods is also appropriate (Goding pp. 71 74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody producing cell lines, which clones can then be propagated indefinitely to provide MAbs. The cell lines may be exploited for MAb production in two basic ways. First, a sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide MAbs in high concentration. Second, the individual cell lines could be cultured in vitro, where the MAbs are naturally secreted into the culture medium from which they can be readily obtained in high concentrations.

Further, expression of antibodies of the invention (or other moieties therefrom) from production cell lines can be enhanced using a number of known techniques. For example, the glutamine synthetase and DHFR gene expression systems are common approaches for enhancing expression under certain conditions. High expressing cell clones can be identified using conventional techniques, such as limited dilution cloning and Microdrop technology. The GS system is discussed in whole or part in connection with European Patent Nos. 0 216 846, 0 256 055, and 0 323 997 and European Patent Application No. 89303964.4.

MAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. In one embodiment, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately 104 times as many antibodies can be produced and screened in a single round, and that new specificities are generated by H and L chain combination which further increases the chance of finding appropriate antibodies. In another example, LEEs or CEEs can be used to produce antigens in vitro with a cell free system. These can be used as targets for scanning single chain antibody libraries. This would enable many different antibodies to be identified very quickly without the use of animals.

Another embodiment of the invention for producing antibodies according to the present invention is found in U.S. Pat. No. 6,091,001, which describes methods to produce a cell expressing an antibody from a genomic sequence of the cell comprising a modified immunoglobulin locus using Cre-mediated site-specific recombination is disclosed. The method involves first transfecting an antibody-producing cell with a homology-targeting vector comprising a lox site and a targeting sequence homologous to a first DNA sequence adjacent to the region of the immunoglobulin loci of the genomic sequence which is to be converted to a modified region, so the first lox site is inserted into the genomic sequence via site-specific homologous recombination. Then the cell is transfected with a lox-targeting vector comprising a second lox site suitable for Cre-mediated recombination with the integrated lox site and a modifying sequence to convert the region of the immunoglobulin loci to the modified region. This conversion is performed by interacting the lox sites with Cre in vivo, so that the modifying sequence inserts into the genomic sequence via Cre-mediated site-specific recombination of the lox sites.

Alternatively, monoclonal antibody fragments encompassed by the present invention can be synthesized using an automated peptide synthesizer, or by expression of full-length gene or of gene fragments in E. coli.

D. Antibody Conjugates

The present invention further provides antibodies against Fbp proteins, polypeptides and peptides, generally of the monoclonal type, that are linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radio-labeled nucleotides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Any antibody of sufficient selectivity, specificity or affinity may be employed as the basis for an antibody conjugate. Such properties may be evaluated using conventional immunological screening methodology known to those of skill in the art. Sites for binding to biological active molecules in the antibody molecule, in addition to the canonical antigen binding sites, include sites that reside in the variable domain that can bind pathogens, B-cell superantigens, the T cell co-receptor CD4 and the HIV-1 envelope (Sasso et al., 1989; Shorki et al., 1991; Silvermann et al., 1995; Cleary et al., 1994; Lenert et al., 1990; Berberian et aL., 1993; Kreier et al., 1991). In addition, the variable domain is involved in antibody self-binding (Kang et al., 1988), and contains epitopes (idiotypes) recognized by anti-antibodies (Kohler et al., 1989).

Certain examples of antibody conjugates are those conjugates in which the antibody is linked to a detectable label. "Detectable labels" are compounds and/or elements that can be detected due to their specific functional properties, and/or chemical characteristics, the use of which allows the antibody to which they are attached to be detected, and/or further quantified if desired. Another such example is the formation of a conjugate comprising an antibody linked to a cytotoxic or anti cellular agent, and may be termed "immunotoxins".

Antibody conjugates are generally preferred for use as diagnostic agents. Antibody diagnostics generally fall within two classes, those for use in in vitro diagnostics, such as in a variety of immunoassays, and/or those for use in vivo diagnostic protocols, generally known as "antibody directed imaging".

Many appropriate imaging agents are known in the art, as are methods for their attachment to antibodies (see, for e.g., U.S. Pat. Nos. 5,021,236; 4,938,948; and 4,472,509, each incorporated herein by reference). The imaging moieties used can be paramagnetic ions; radioactive isotopes; fluorochromes; NMR-detectable substances; X-ray imaging.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium186, rhenium188, $^{75}$selenium, $^{35}$sulphur, technicium99m and/or yttrium$^{90}$. $^{125}$I, is often being preferred for use in certain embodiments, and technicium$^{99m}$ and/or indium$^{111}$ are also often preferred due to their low energy and suitability for long range detection. Radioactively labeled monoclonal antibodies of the present invention may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the invention may be labeled with technetium99m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present invention are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter & Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; and Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938, 948, each incorporated herein by reference). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'shannessy et al., 1987). This approach has been reported to produce diagnostically and therapeutically promising antibodies which are currently in clinical evaluation.

In another embodiment of the invention, the anti-Fbp antibodies are linked to semiconductor nanocrystals such as those described in U.S. Pat. Nos. 6,048,616; 5,990,479; 5,690,807; 5,505,928; 5,262,357 (all of which are incorporated herein in their entireties); as well as PCT Publication No. 99/26299 (published May 27, 1999). In particular, exemplary materials for use as semiconductor nanocrystals in the biological and chemical assays of the present invention include, but are not limited to those described above, including group II-VI, III-V and group IV semiconductors such as ZnS, ZnSe, ZnTe, CdS, CdSe, CdTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlS, AlP, AlSb, PbS, PbSe, Ge and Si and ternary and quaternary mixtures thereof. Methods for linking semiconductor nanocrystals to antibodies are described in U.S. Pat. Nos. 6,630,307 and 6,274,323.

E. Immunodetection Methods

In still further embodiments, the present invention concerns immunodetection methods for binding, purifying, removing, quantifying and/or otherwise generally detecting biological components such as immunoreactive Fbp polypeptides. The Fbp antibodies prepared in accordance with the present invention may be employed to detect wild type and/or mutant Fbp proteins, polypeptides and/or peptides. The use of wild-type and/or mutant Fbp-specific antibodies is contemplated. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle MH and Ben-Zeev 0, 1999; Gulbis B and Galand P, 1993; De Jager R et al., 1993; and Nakamura et al., 1987, each incorporated herein by reference.

In general, the immunobinding methods include obtaining a sample suspected of comprising Fbp protein, polypeptide and/or peptide, and contacting the sample with a first anti-Fbp antibody in accordance with the present invention, as the case may be, under conditions effective to allow the formation of immunocomplexes.

These methods include methods for purifying wild type and/or mutant Fbp proteins, polypeptides and/or peptides as may be employed in purifying wild type and/or mutant Fbp proteins, polypeptides and/or peptides from patients' samples and/or for purifying recombinantly expressed wild type or mutant Fbp proteins, polypeptides and/or peptides. In these instances, the antibody removes the antigenic wild type and/or mutant Fbp protein, polypeptide and/or peptide component from a sample. The antibody will preferably be linked to a solid support, such as in the form of a column matrix, and the sample suspected of containing the wild type or mutant Fbp protein antigenic component will be applied to the immobilized antibody. The unwanted components will be washed from the column, leaving the antigen immunocomplexed to the immobilized antibody, which wild type or mutant Fbp protein antigen is then collected by removing the wild type or mutant Fbp protein and/or peptide from the column.

The immunobinding methods also include methods for detecting and quantifying the amount of a wild type or mutant Fbp protein reactive component in a sample and the detection and quantification of any immune complexes formed during the binding process. Here, one would obtain a sample suspected of comprising a wild type or mutant Fbp protein and/or peptide or suspected of comprising an *E. canis* organism, and contact the sample with an antibody against wild type or mutant Fbp, and then detect and quantify the amount of immune complexes formed under the specific conditions.

In terms of antigen detection, the biological sample analyzed may be any sample that is suspected of containing a wild type or mutant Fbp protein-specific antigen, such as a specimen, a homogenized tissue extract, a Fbp cell, separated and/or purified forms of any of the above wild type or mutant Fbp protein-containing compositions, or even any biological fluid that comes into contact with an *E. canis* organism upon infection.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any Fbp protein antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags.

U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The Fbp antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

The immunodetection methods of the present invention have evident utility in the diagnosis and prognosis of conditions such as various forms of hyperproliferative diseases, such as cancer, including leukemia, for example. Here, a biological and/or clinical sample suspected of containing a wild type or mutant Fbp protein, polypeptide, peptide and/or mutant is used. However, these embodiments also have applications to non-clinical samples, such as in the titering of antigen or antibody samples, for example in the selection of hybridomas.

In the clinical diagnosis and/or monitoring of patients with various forms of hyperproliferative disease, such as cancer, for example, leukemia, the detection of Fbp mutant, and/or an alteration in the levels of Fbp, in comparison to the levels in a corresponding biological sample from a normal subject is indicative of a patient with hyperproliferative disease, such as cancer, including leukemia. However, as is known to those of skill in the art, such a clinical diagnosis would not necessarily be made on the basis of this method in isolation. Those of skill in the art are very familiar with differentiating between significant differences in types and/or amounts of biomarkers, which represent a positive identification, and/or low level and/or background changes of biomarkers. Indeed, background expression levels are often used to form a "cut-off" above which increased detection will be scored as significant and/or positive.

F. ELISAs

As detailed above, immunoassays, in their most simple and/or direct sense, are binding assays. Certain preferred immunoassays are the various types of enzyme linked immunosorbent assays (ELISAs) and/or radioimmunoassays (RIA) known in the art. Immunohistochemical detection using tissue sections is also particularly useful. However, it will be readily appreciated that detection is not limited to such techniques, and/or western blotting, dot blotting, FACS analyses, and/or the like may also be used.

In one exemplary ELISA, the anti-Fbp antibodies of the invention are immobilized onto a selected surface exhibiting protein affinity, such as a well in a polystyrene microtiter plate. Then, a test composition suspected of containing the wild type and/or mutant Fbp protein antigen, such as a clinical sample, is added to the wells. After binding and/or washing to remove non-specifically bound immune complexes, the bound wild type and/or mutant Fbp protein antigen may be detected. Detection is generally achieved by the addition of another anti Fbp antibody that is linked to a detectable label. This type of ELISA is a simple "sandwich ELISA". Detection may also be achieved by the addition of a second anti-Fbp antibody, followed by the addition of a third antibody that has binding affinity for the second antibody, with the third antibody being linked to a detectable label.

In another exemplary ELISA, the samples suspected of containing the wild type and/or mutant Fbp protein antigen are immobilized onto the well surface and/or then contacted with the anti-Fbp antibodies of the invention. After binding and/or washing to remove non-specifically bound immune complexes, the bound anti-Fbp antibodies are detected. Where the initial anti-Fbp antibodies are linked to a detectable label, the immune complexes may be detected directly. Again, the immune complexes may be detected using a second antibody that has binding affinity for the first anti Fbp antibody, with the second antibody being linked to a detectable label.

Another ELISA in which the wild type and/or mutant Fbp proteins, polypeptides and/or peptides are immobilized, involves the use of antibody competition in the detection. In this ELISA, labeled antibodies against wild type or mutant Fbp protein are added to the wells, allowed to bind, and/or detected by means of their label. The amount of wild type or mutant Fbp protein antigen in an unknown sample is then determined by mixing the sample with the labeled antibodies against wild type and/or mutant Fbp before and/or during incubation with coated wells. The presence of wild type and/or mutant Fbp protein in the sample acts to reduce the amount of antibody against wild type or mutant protein available for binding to the well and thus reduces the ultimate signal. This is also appropriate for detecting antibodies against wild type or mutant Fbp protein in an unknown sample, where the unlabeled antibodies bind to the antigen-coated wells and also reduces the amount of antigen available to bind the labeled antibodies.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

G. Immunohistochemistry

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in 70° C. isopentane; cutting the plastic capsule and/or removing the frozen cylinder of tissue; securing the tissue cylinder on a cryostat microtome chuck; and/or cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections.

H. Immunoelectron Microscopy

The antibodies of the present invention may also be used in conjunction with electron microscopy to identify intracellular tissue components. Briefly, an electron-dense label is conjugated directly or indirectly to the anti-Fbp antibody. Examples of electron-dense labels according to the invention are ferritin and gold. The electron-dense label absorbs electrons and can be visualized by the electron microscope.

I. Immunodetection Kits

In still further embodiments, the present invention concerns immunodetection kits for use with the immunodetection methods described above. As the Fbp antibodies are generally used to detect wild type and/or mutant Fbp proteins, polypeptides and/or peptides, the antibodies will preferably be included in the kit. However, kits including both such components may be provided. The immunodetection kits will thus comprise, in suitable container means, a first antibody that binds to a wild type and/or mutant Fbp protein, polypeptide and/or peptide, and/or optionally, an immunodetection reagent and/or further optionally, a wild type and/or mutant Fbp protein, polypeptide and/or peptide.

In preferred embodiments, monoclonal antibodies will be used. In certain embodiments, the first antibody that binds to the wild type and/or mutant Fbp protein, polypeptide and/or peptide may be pre-bound to a solid support, such as a column matrix and/or well of a microtitre plate.

The immunodetection reagents of the kit may take any one of a variety of forms, including those detectable labels that are associated with and/or linked to the given antibody. Detectable labels that are associated with and/or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and/or all such labels may be employed in connection with the present invention.

The kits may further comprise a suitably aliquoted composition of the wild type and/or mutant Fbp protein, polypeptide and/or polypeptide, whether labeled and/or unlabeled, as may be used to prepare a standard curve for a detection assay. The kits may contain antibody-label conjugates either in fully conjugated form, in the form of intermediates, and/or as separate moieties to be conjugated by the user of the kit. The components of the kits may be packaged either in aqueous media and/or in lyophilized form.

The container means of the kits will be suitable housed and will generally include at least one vial, test tube, flask, bottle, syringe and/or other container means, into which the antibody may be placed, and/or preferably, suitably aliquoted. Where wild type and/or mutant Fbp protein, polypeptide and/or peptide, and/or a second and/or third binding ligand and/or additional component is provided, the kit will also generally contain a second, third and/or other additional container into which this ligand and/or component may be placed. The kits of the present invention will also typically include a means for containing the antibody, antigen, and/or any other reagent containers in close confinement for commercial sale. Such containers may include injection and/or blow-molded plastic containers into which the desired vials are retained.

VII. Pharmaceutical Preparations

It is also contemplated that pharmaceutical compositions may be prepared using the novel proteins of the present invention. In such a case, the pharmaceutical composition comprises the novel active composition of the present invention and a pharmaceutically acceptable carrier. A person having ordinary skill in this art would readily be able to determine, without undue experimentation, the appropriate dosages and routes of administration of the active component of the present invention.

The phrase "pharmaceutically acceptable" refers to molecular entities and compositions that do not produce an allergic or similar untoward reaction when administered to a subject. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

In general, a pharmaceutical composition of the present invention may comprise an E. canis Fbp polypeptide, polynucleotide, or antibody.

A protein may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media, which can be employed, will be known to those of skill in the art in light of present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Pharmaceutical compositions of the present invention comprise an effective amount of one or more agents that target Fbp or the secretion thereof or additional agent dissolved or dispersed in a pharmaceutically acceptable carrier. The phrases "pharmaceutical," "pharmaceutically acceptable," or "pharmacologically acceptable" refers to molecular entities and compositions that do not produce an adverse, allergic or other untoward reaction when administered to an animal, such as, for example, a human, as appropriate. The preparation of a pharmaceutical composition that contains at least one agent that targets Fbp or the secretion thereof and/or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The invention may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The invention may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the composition is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations that are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

VIII. Kits of the Invention

In particular embodiments of the invention, there is a kit housed in a suitable container. The kit may be suitable for diagnosis, treatment, and/or protection for an individual from *Ehrlichia*, such as *Ehrlichia canis*. In particular embodiments, the kit comprises in a suitable container an agent that targets an *E. canis* Fbp antigen. The agent may be an antibody, a small molecule, a polynucleotide, a polypeptide, a peptide, or a mixture thereof. The agent may be provided in the kit in a suitable form, such as sterile, lyophilized, or both, for example. In particular embodiments, the kit comprises an antibody against SEQ ID NO:2 or related proteins thereof, the kit comprises SEQ ID NO:2 or related proteins thereof, the kit comprises SEQ ID NO:1 or one or more other sequences that encode SEQ ID NO:2 or related proteins thereof, or a combination thereof.

The kit may further comprise one or more apparatuses for delivery of a composition to an individual in need thereof. The apparatuses may include a syringe, eye dropper, needle, biopsy tool, scoopula, catheter, and so forth.

In embodiments wherein the kit is employed for a diagnostic purpose, the kit may further provide one or more detection compositions or apparatuses for identifying an *E. canis* Fbp antigen. Such an embodiment may employ a detectable label, such as for an antibody, for example, and the label may be fluorescent, chemiluminescent, or calorimetric, for example.

IX. EXAMPLES

The following examples are given for the purpose of illustrating various embodiments of the invention and are not meant to limit the present invention in any fashion. The present examples, along with the methods, procedures, treatments, molecules, and specific compounds described herein are presently representative of preferred embodiments. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

Example 1

Identification, Cloning and Expression of the *E. Canis* Immunoreactive Fbp

Discovery of an immunoreactive *E. canis* Fbp. Expression clones from a HpaII *E. canis* genomic library were screened as previously described (McBride et al., 2001). A positive clone with a 3-kb insert contained a complete 1,044 bp open reading frame (ORF) encoding a predicted protein with a molecular mass of 38.8 kDa with homology to periplasmic ferric binding proteins (Fbp) characterized in several gram-negative organisms. An N-terminal signal sequence of 27 amino acids on the *E. canis* Fbp was identified by the SignalP prediction server (Nielsen et al., 1997). The molecular mass of the mature protein is predicted to be 35.8 kDa. This 3-kb clone also contained a partial ORF upstream of fbp with homology to the surface protein p106 of *E. chaffeensis* (Yu et al., 1999).

Identification of native *E. canis* Fbp protein. Rabbit serum raised against the recombinant Fbp protein was used to identify the corresponding native protein in *E. canis* whole cell lysates by Western blotting. The antiserum recognized a native *E. canis* protein with a molecular mass of 38 kDa corresponding to that predicted by the amino acid sequence (FIG. 1). The protein recognized by the anti-Fbp antiserum identified an immunoreactive *Ehrlichial* protein weakly recognized by antibodies in serum from an *E. canis*-infected dog (FIG. 1).

Immunoreactivity of *E. canis* Fbp. The expressed recombinant Fbp fusion protein exhibited a molecular mass of approximately 40 kDa and reacted with anti-*E. canis* antiserum from several experimentally infected dogs (data not shown). The reactivity of sera from *E. canis* infected dogs against denatured Fbp epitopes was weak. To determine if a conformational epitope contributed to the immunoreactivity that led to the identification of Fbp, the recombinant Fbp was reacted with sera by dot blot under native conditions (FIG. 2). The recombinant Fbp reacted with *E. canis* antisera by dot blot under both native conditions and in the presence of reducing agents without SDS (FIG. 2). Fbp incubated in the presence of SDS exhibited reduced immunoreactivity to anti-*E. canis* antibodies in serum collected from dogs on day 28 (FIG. 2*a*) and 42 (FIG. 2*b*) post-infection. The denatured (SDS-exposed) Fbp had increased reactivity with serum from day 42 post-infection compared to day 28, but was still substantially weaker than native Fbp, indicating that the immunoreactivity of Fbp is dependent on a conformational epitope that is sensitive to SDS and unaffected by reducing agents. Pre-immune serum from each of the experimentally infected dogs tested negative for Fbp binding (data not shown). In addition, both anti-*E. canis* and anti-*E. chaffeensis* Fbp antisera exhibited cross-reactivity with the orthologous Fbp of the other species (data not shown).

Example 2

Fbp Homology and Modeling of the *E. Canis* Fbp Protein

Figure 3:
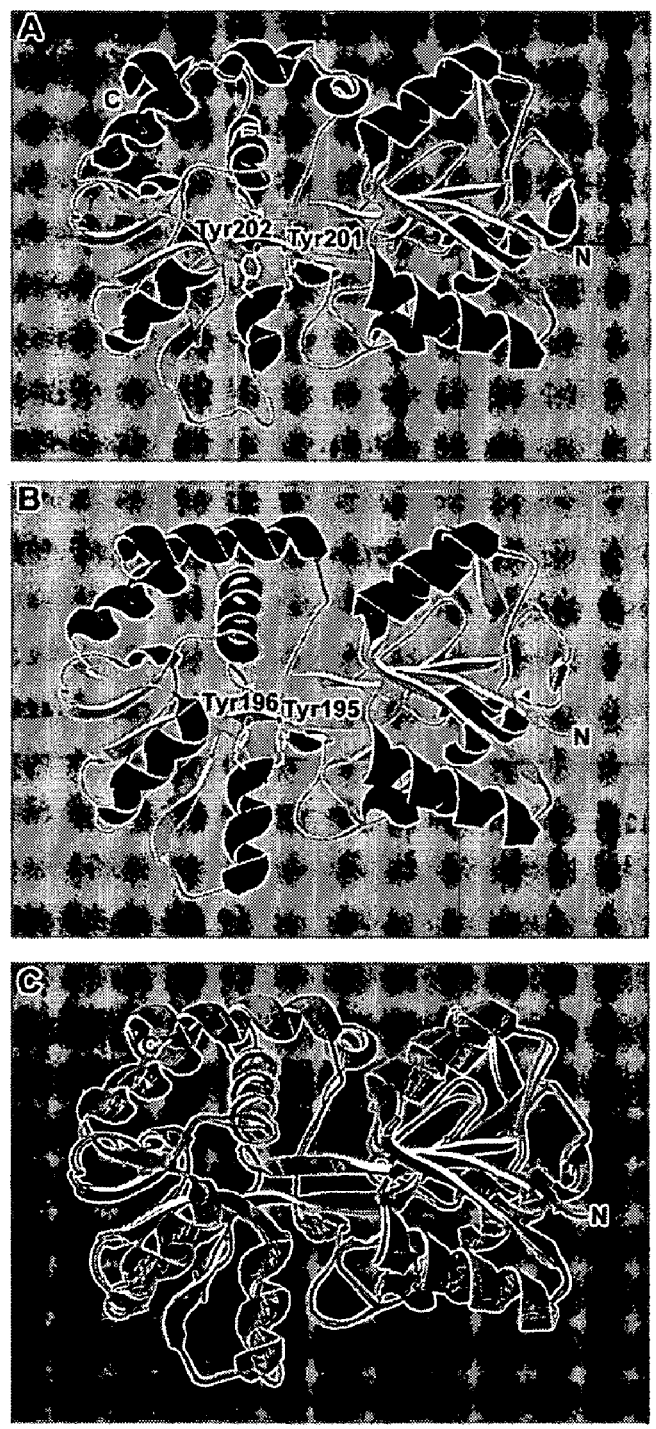
FIG. 3 provides exemplary three-dimensional structural modeling of *E. canis* Fbp using the Swiss-Model. The putative structure of *E. canis* Fbp (A) is compared to the crystal structure of *N. gonorrhoeae* Fbp (B). Colors correspond to secondary structure where red designates an alpha helix and yellow a β-pleated sheet. (C) Structural overlay of *E. canis* Fbp (green) with the crystal structure of *N. gonorrhoeae* Fbp (blue).

Fbp homology and modeling of *Ehrlichia* Fbp structure. BLAST analysis of the protein sequence of *E. canis* Fbp determined that it shares homology with a family of known ferric binding proteins. This family includes bacterial Fbps from *Neisseria gonorrhoeae* and *Haemophilus influenzae*, both of which share ~28% homology with *E. canis* Fbp, and an Fbp from *Mannheimia (Pasteurella) haemolytica* which shares 40% homology. The amino acid sequence of the *E. canis* Fbp included two adjacent tyrosines near position 200 of the mature protein, which are key components of the iron binding potential of the Fbp family (Bruns et al., 1997; Shouldice et al., 2003). The amino acid sequence of *E. canis* Fbp also maintains a basic amino acid at Lys14 that aligns with the important His9 of these proteins from *N. gonorrhoeae* and *H. influenzae* (Bruns et al., 1997). The crystal structure of *M. haemolytica* predicted an octahedral means of iron coordination involving eight amino acids (Shouldice et al., 2003), six of which (the dityrosyl motif at positions 201-202, another key tyrosine at position 145, and arginines at positions 13, 105, and 139) are conserved with *E. canis* Fbp (Shouldice et al., 2003). An orthologous gene from *E. chaffeensis* has been previously described as a putative ferric binding protein, but was not immunoreactive and its iron binding capabilities were not determined (Yu et al., 1999). The *E. muris* fbp gene (reported herein) and *E. chaffeensis* fbp exhibited 87% homology with the *E. canis* fbp. The crystal structures of the Fbps from *N. gonorrhoeae, H. influenzae,* and *M. haemolytica* are known (Bruns et al., 2001; Bruns et al., 1997; Shouldice et al., 2003a; Shouldice et al., 2003b), which allowed modeling of the primary sequence of *E. canis* Fbp against the crystal structures using Swiss-Model. The model predicts that the *E. canis* Fbp exhibits the characteristic two domain structure connected by a hinge region of antiparallel β-strands, as seen in the Fbps and similar to the lobes of mammalian transferrin (Bruns et al., 1997; Nowalk et al., 1994) (FIG. 3). As with other bacterial Fbp, the two domains are made up of a central β-sheet surrounded by multiple α-helices (FIG. 3).

Example 3

Genomic Organization of the *E. Canis* Iron Acquisition Proteins

Figure 4:
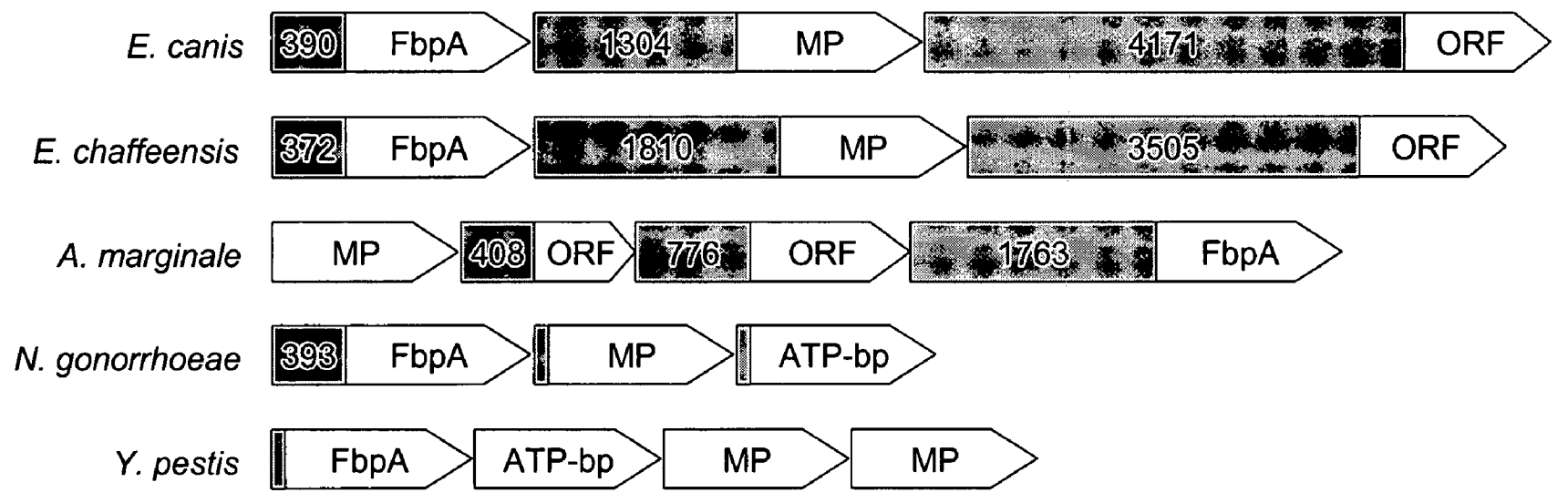

The known Fbp family members are a part of a 4-kb iron-regulated operon which includes the functionally related membrane permease and an ATP-binding protein. The members of these iron transporting operons are separated by small intergenic sequences, 56 bp between fbpA and fbpB and 21 bp between fbpB and fbpC in the *Neisseria gonorrhoeae* system (Adhikari et al., 1996), and no intergenic regions in the *Yersinia pestis* yfeABCD system (Bearden et al., 1998). Examining the neighboring genes from available genome of the *Ehrlichia canis* fbp identifies a putative membrane permease downstream from fbp, but separated by 1.304 kb (FIG. 4). A similar study of the *E. chaffeensis* fbp region places the putative membrane permease 1.81 kb downstream of fbp (FIG. 4). Interestingly, the related rickettsial organism *Anaplasma marginale* genome positions this putative membrane permease upstream of the fbp gene by 5.5 kb and has two ORFs that are not homologous to other iron acquisition proteins (FIG. 4). Both genomes contain functionally unrelated ORFs on the negative strand DNA located in the intergenic space between fbp and the putative membrane permease (not shown). The search for fbp and neighboring genes in *Wolbachia pipiens* and *Neorickettsia sennetsu* found the presence of the fbp ortholog, but absence of genes encoding both the membrane permease and an ATP-binding protein within 5 kb of fbp. Downstream (>4 kb) from the putative *Ehrlichia* membrane permease, a gene encoding an ATP-binding protein is not present, and the closest major ORF is ~7 kb downstream from fbp. The operon system of *Neisseria gonorrhoeae* has been demonstrated to be under the control of the iron regulatory element Fur (ferric uptake regulator)(Desai et al., 1996) and putative Fur binding sites have been found in other Fbp systems, such as the *Y pestis* YfeABCD (Bearden et al., 1998). Analysis of the sequence upstream of *E. canis* fbp identified a putative Fur binding site at position 136 from the start with a sequence of TATTATTTAATGTAATTATG (SEQ ID NO:15) that contains two copies of the *E. coli* Fur recognition consensus ATA/TAT (Escolar et al., 1999). Another putative Fur box containing one copy of the consensus, with sequence AATTATTTTGGAAAAATAAG (SEQ ID NO:16), is located 85 from the beginning of the putative membrane permease gene.

Example 4

Loss of Fbp Operon Regulation in *E. Canis*

Figure 5:
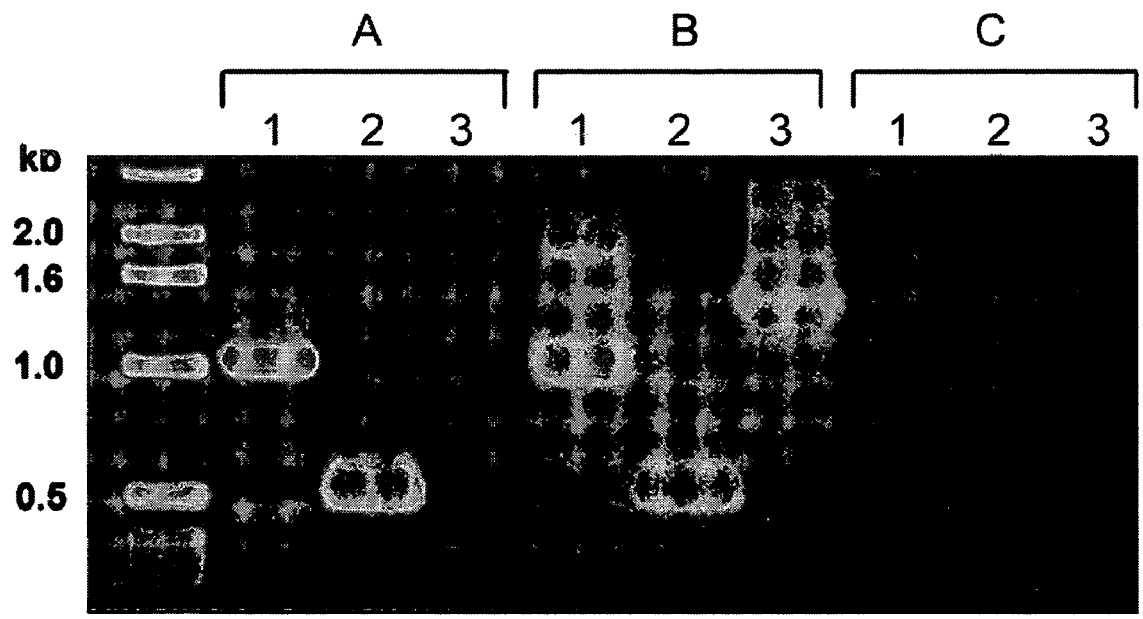
FIG. 5 demonstrates RT-PCR of 1) *E. canis* fbp, 2) *E. canis* membrane permease, 3) intergenic region spanning from the 3' end of fbp to the 5' start of membrane permease with A) RNA from *E. canis* infected DH82 cells, B) *E. canis* genomic DNA, C) no RT control.

With the loss of conserved genomic organization with the associating membrane permease and ATP-binding protein genes, we hypothesized that the operon regulation had been lost in *Ehrlichia*. To study this, RT PCR was performed with primers for the 1 kb fbp gene, a 500 bp region of the downstream membrane permease, and with primers designed to span ~1.4 kb from the 3' end of fbp over the intergenic region and 127 bp into the membrane permease gene. If transcription was occurring in a polycistronic fashion, then all three would be detected by RT-PCR. Transcripts of fbp and membrane permease could be detected, but not a polycistronic transcript containing both genes (FIG. 5A). These transcripts were specific for *E. canis* infected DH82 cells and were not seen with uninfected host DH82 cell RNA (data not shown). Controls with genomic DNA could amplify the product under the conditions used (FIG. 5B).

Example 5

Iron Binding by the *E. Canis* Fbp

Ferric binding proteins exhibit a spectral peak in the 400-500 nm range when bound to iron (Kirby et al., 1998). Following recombinant protein purification, the Fbp exhibited a visible intense red color. The absorbance of the protein was determined with a spectrophotometric spectral scan, and an absorbance peak at 410 nm was observed with Fbp (FIG. 6a, top). Addition of the iron chelator sodium citrate competed away the iron, eliminating the absorbance peak (FIG. 6a, bottom). In addition, recombinant iron-bound holo-Fbp turned blue with the iron-specific Ferene S stain (Chung, 1985), indicative of iron binding (FIG. 6b). The iron-free apo form of Fbp did not stain positive with Ferene S (FIG. 6b). Ferene S, which is specific for iron(II), did not turn holo-Fbp blue in the absence of reducing agent thioglycolic acid, evidence that the bound iron is the iron(III) form and not iron(II) (FIG. 6b).

Example 6

Cellular Location of the E. Canis Fbp and E. Chaffeensis Fbp Protein

Figure 7:
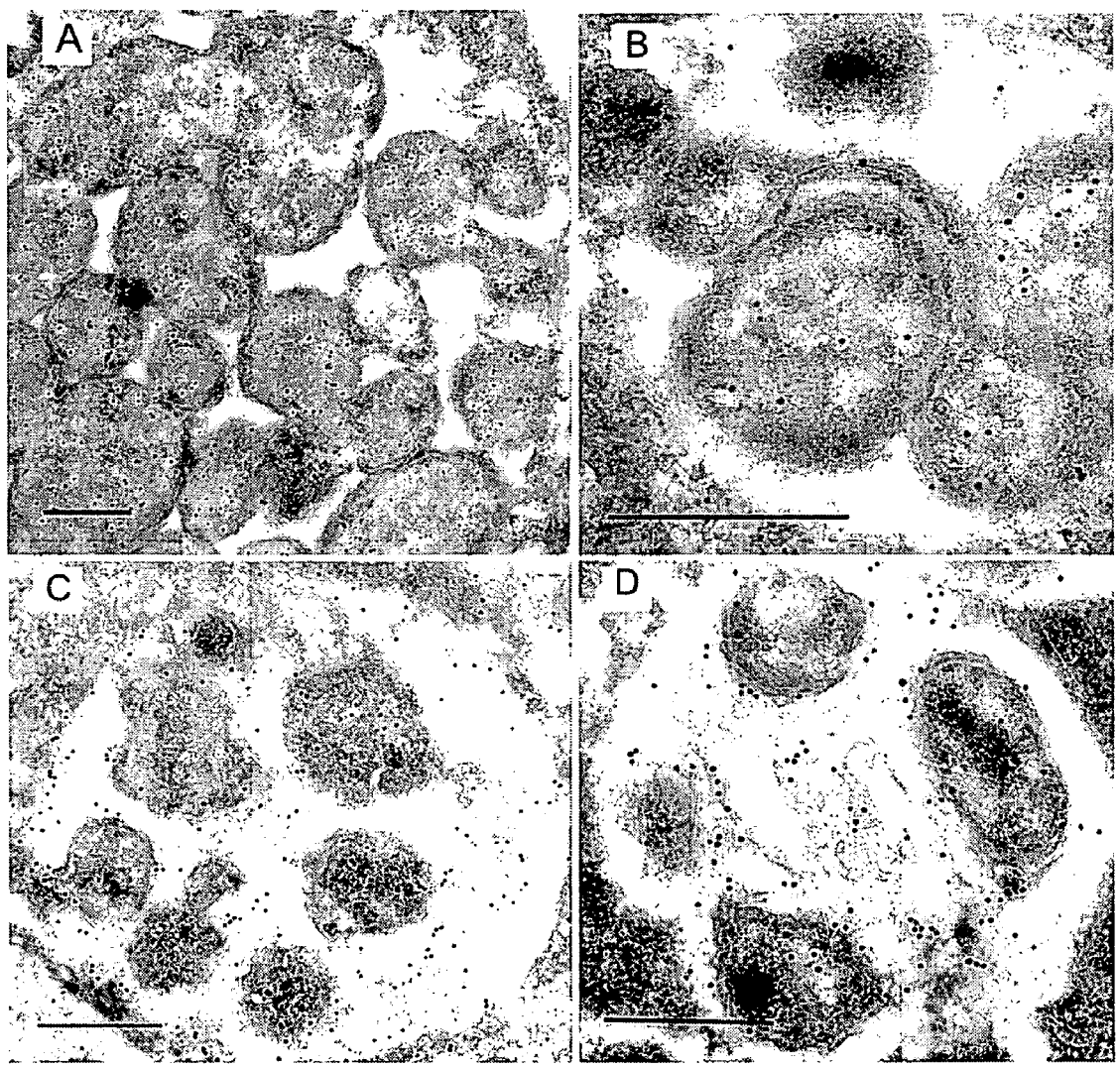
FIG. 7 illustrates a representative immunogold-labeled electronmicrograph of *E. canis* and *E. chaffeensis* with anti-*E. canis* recombinant Fbp. Localization of Fbp in the (A) *E. canis* and (B) *E. chaffeensis* reticulate morphological form. Localization of Fbp in the (C) *E. canis* and (D) *E. chaffeensis* dense-cored morphological form. The distance bar represents 0.5 μm.

Ultrathin sections containing E. canis and E. chaffeensis in infected DH82 cells were incubated with antibodies against E. canis rFbp and visualized with colloidal gold particles by immunoelectron microscopy. Ehrlichia exist in two distinct morphological forms (Popov et al., 1995), the reticulate and dense-cored. Fbp was found primarily in the cytoplasm of the reticulate form in both species, with some localization in the periplasmic space and on the bacterial surface (FIGS. 7A and B). The dense-cored form of the bacteria also exhibited Fbp localization in the cytoplasm (FIGS. 7C and D), but Fbp was also found extracellularly on the intramorular fibers in E. canis and E. chaffeensis morulae containing the dense-cored form (FIGS. 7C and D).

Example 7

Cloning, Expression and Immunoreactivity of the Fbp Gene

The E. canis fbp gene was PCR-amplified with primers corresponding to nucleotides 82 to 101 within the ORF and a region 198 bp downstream of the open reading frame and degenerate primers corresponding to bp 1 through 20 (forward) and 1025 through 1044 (reverse) for the conserved regions in the coding regions of E. canis Fbp. The PCR-amplified product was cloned into a universal TOPO TA Echo vector (pUni, Invitrogen, Carlsbad, Calif.) and then recombined with acceptor vector pRSET, designed to produce proteins with native C terminus and an N-terminal polyhistidine region for purification. The plasmid containing the cloned fbp gene was used to transform TOP10 E.coli (Invitrogen, Carlsbad, Calif.) and positive transformants were screened by PCR for presence of insert as well as its orientation. The selected transformants containing the plasmid with insert were then sequenced to confirm the correct reading frame of fbp gene.

Expression of the recombinant Fbp was performed in BL21(DE3)/pLysS E.coli (Invitrogen) after induction with 1.0 mM IPTG (isopropyl-β-D-thiogalactopyranoside) for 3 h at 37° C. Recombinant Fbp was purified under native conditions by sonicating the pelleted bacteria and then resuspended in PBS (phosphate buffered saline). The lysate was centrifuged to remove insoluble material by centrifugation and then loaded onto an equilibrated nickel-nitrilotriacetic acid (Ni-NTA) agarose column (Qiagen, Valencia, Calif.). The bound recombinant protein was washed with five column volumes of increasing concentrations 0.8, 8 mM, and 40 mM) of imidazole (Sigma-Aldrich, St. Louis, Mo.) and eluted with PBS plus 80 mM imidazole. Purified recombinant protein was then dialyzed by ultrafiltration with PBS using Microcon centrifugal concentrators with a 30kDa cutoff (Millipore, Billerica, Mass.). Purified E. canis antigens were separated by SDS-polyacrylamide gel electrophoresis (SDS-PAGE) before being used for Western blots where the primary antibodies were diluted (1:500).

The expressed recombinant Fbp fusion protein exhibited a molecular mass of 40 kDa and reacted with anti-E. canis antiserum from experimentally infected dogs. However, the reactivity of sera from E. canis infected dogs against linear Fbp epitopes was variable. In order to determine if the variability in the reactivity of sera from E. canis infected dogs against linear Fbp epitopes was due to conformational epitope, the dot blot analyses was performed under native, denaturing (protein plus 0.1% w/v SDS), reduced (protein with 50 mM dithiothreitol diluted from the NuPAGE 10× reducing agent (Invitrogen, Carlsbad, Calif.)) and in the presence of both denaturing and reduced conditions (protein with a combination of SDS plus reducing agent). The recombinant proteins were not well recognized under denaturing conditions with antiserum collected on day 28 post-infection (FIG. 5A). However, the serum collected on day 42 post-infection recognized the protein under denaturing conditions, but the degree of recognition was lower than that under non-denaturing conditions (FIG. 5B).

Example 8

Identification of Native E. Canis Fbp Protein

Figure 6:
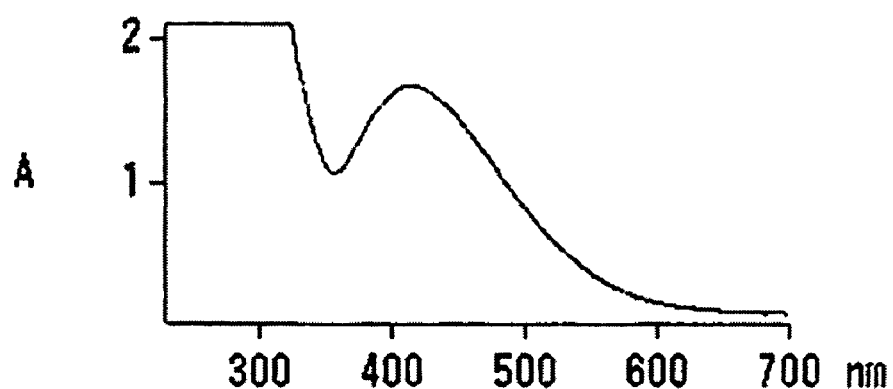
FIG. 6 shows iron binding of *E. canis* Fbp. (A) Absorbance of *E. canis* Fbp in the iron-bound (holo) (top) and the apo (iron-free state) forms (bottom). (B) Positive Ferene S staining for iron of recombinant *E. canis* holo-Fbp (Fbp-H), but not the Fbp-apo form (Fbp-A). In the absence of reducing agent thioglycolic acid, holo-Fbp did not stain positive by Ferene S, demonstrating the bound iron is Fe(III) and not Fe(II).
Figure 6:
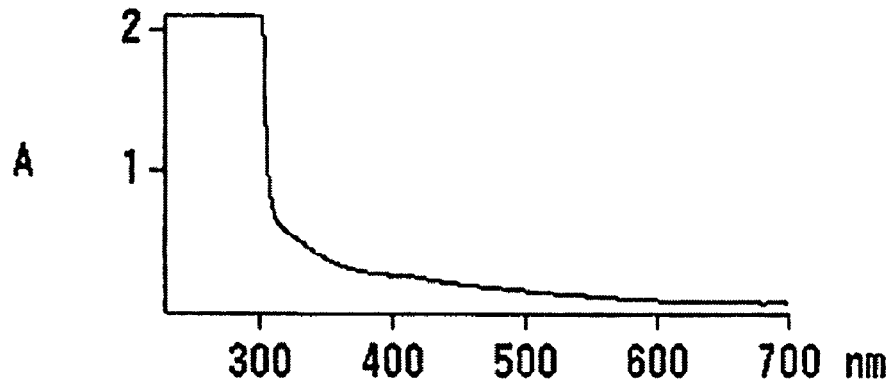
Figure 6:

Rabbit serum raised against the recombinant Fbp protein was used to determine the molecular weight of the native protein antigen by Western blot analysis (FIG. 6). The rabbit anti-E. canis recombinant Fbp was generated by immunizing a New Zealand White rabbit (Myrtle's Rabbitry Inc., Thompson Station, Tenn.) with recombinant E. canis Fbp protein. The recombinant protein (100 μg in 0.5 mL) was mixed with equal volume of Freund's complete adjuvant (Sigma, St. Louis, Mo.) for the first injection and with Freund's incomplete adjuvant for the subsequent injections. The rabbit was immunized subcutaneously twice at 2 week intervals.

The antiserum recognized a native E. canis protein with a molecular weight (38 kDa) that was consistent with the predicted amino acid sequence. The protein recognized by the α-Fbp antiserum identified an immunoreactive Ehrlichial protein weakly recognized by E. canis infected dog serum (FIG. 6).

Example 9

Significance of the Present Invention

Although iron binding proteins have been identified in numerous extracellular bacteria, the discovery of a functional ferric binding protein in Ehrlichia canis represents the first such description in an obligately intracellular bacterium. The identification of ferric binding proteins in Ehrlichia represents the first step in understanding the mechanisms of iron acquisition by the organism as well as other obligate intracellular bacteria. In the other systems, the Fbp functions as the periplasmic transporter after other proteins have acquired the iron from the extracellular iron binding protein transferrin. Ehrlichia are not likely to obtain iron from the extracellular milieu, but after entering the host cell. Ehrlichia upregulate the transferrin receptor and recruit it to the intracytoplasmic vacuole (morula) (Barnewall et al., 1997). It is likely that iron acquisition by Ehrlichia occurs within the morula.

Large intergenic sequences between fbp and the putative Ehrlichia membrane permease suggested that Ehrlichia spp. fbp is not part of an operon iron acquisition system identified in other gram-negative bacteria, which was confirmed by RT-PCR. The absence of an ATP-binding protein in the region was also noted, although mutational analysis of the gene encoding the ATP-binding protein of the Neisseria gonorrhoeae operon suggests that this protein is not essential for functional iron acquisition (Sebastian and Genco, 1999). Genetic analysis of fbp from related rickettsial organisms *Anaplasma marginale, Wolbachia pipiens*, and *Neorickettsia sennetsu* also demonstrated the lack of an operon including a change in the fbp membrane permease gene order (*Anaplasma*) or the absence of the associated genes encoding the membrane permease and ATP-binding protein in the region (*Wolbachia* and *Neorickettsia*). Only one copy of the fbp gene is found in each of these genome sequences. The loss of the fbp operon in *Ehrlichia* spp. suggests that the *Ehrlichial* Fbp plays a distinct and potentially more direct role in the acquisition and transport of iron.

*E. canis* Fbp was found to share protein sequence homology with known iron binding proteins from other pathogens. Modeling of the *E. canis* Fbp against the known Fbp crystal structures of *Neisseria gonorrhoeae, Haemophilus influenzae*, and *Mannheimia haemolytica* predicted that the *E. canis* Fbp contained the two domain structure connected by a hinge as seen in these other proteins. *E. canis* Fbp also contains two key tyrosines shared by all members of the Fbp family and required for iron coordination (Shouldice et al., 2003) and thus appears to conform well to this known iron binding motif. Iron binding experiments with *E. canis* Fbp demonstrated that it does in fact bind iron(III). This trait is shared with other Fbp and demonstrates that *Ehrlichia* Fbp could function by binding iron(III) dissociated from transferrin recruited to the morulae (Barnewall et al., 1997). The *E. canis* fbp gene contained a putative iron regulatory element Fur (ferric uptake regulator) binding site at position 136 from the start that contained two copies of the *E. coli* Fur recognition consensus sequence, suggesting that it is likely regulated in response to the availability of iron. Another putative Fur box containing only one copy of the consensus sequence is located −85 from the beginning of the putative membrane permease gene, but it is not yet known whether this gene is regulated by Fur or if it plays a coordinated role with Fbp in *Ehrlichia* iron acquisition.

By immunoelectron microscopy, the present inventors have determined that Fbp is located in the cytoplasm, the periplasm, and surface of *Ehrlichia*. Yu et al. reported the localization of *E. chaffeensis* Fbp to the cytoplasm and periplasmic space (Yu et al., 1999). The present inventors also report this localization in the reticulate form, but also detected extracellular Fbp on fibers within morulae containing the dense-cored form that were not observed by Yu et al. With Fbp localization in all parts of the bacteria, it is possible that the protein itself can shuttle free iron into the bacteria for utilization. The *E. canis* Fbp protein contained a signal sequence suggesting that it could be transported to the periplasm, outer membrane, or secreted. The present inventors have demonstrated that in morulae containing dense-cored forms of *Ehrlichiae*, Fbp is located on the surface of the organism, in the extracellular space, and on the morula membrane. The metabolic activity of the two morphological forms of *Ehrlichia* has not been determined, but Fbp may be secreted extracellularly to bind to free iron and prevent toxicity while the bacteria are metabolically inactive. Several gram-negative bacteria have been discovered to produce iron binding proteins, such as ferritin, bacterioferritin, and Dps (DNA-binding protein from starved-cells) to reduce the damage from oxidative stress (Altuvia et al., 1994; Frazier et al., 1993; Ishikawa et al., 2003; Romao et al., 2000; Touati et al., 1995; Yariv et al., 1981; Zhao et al., 2002). The extracellular localization of the *Ehrlichia* Fbp indicates that it functions in a manner different than described for other gram-negative systems.

Figure 2:
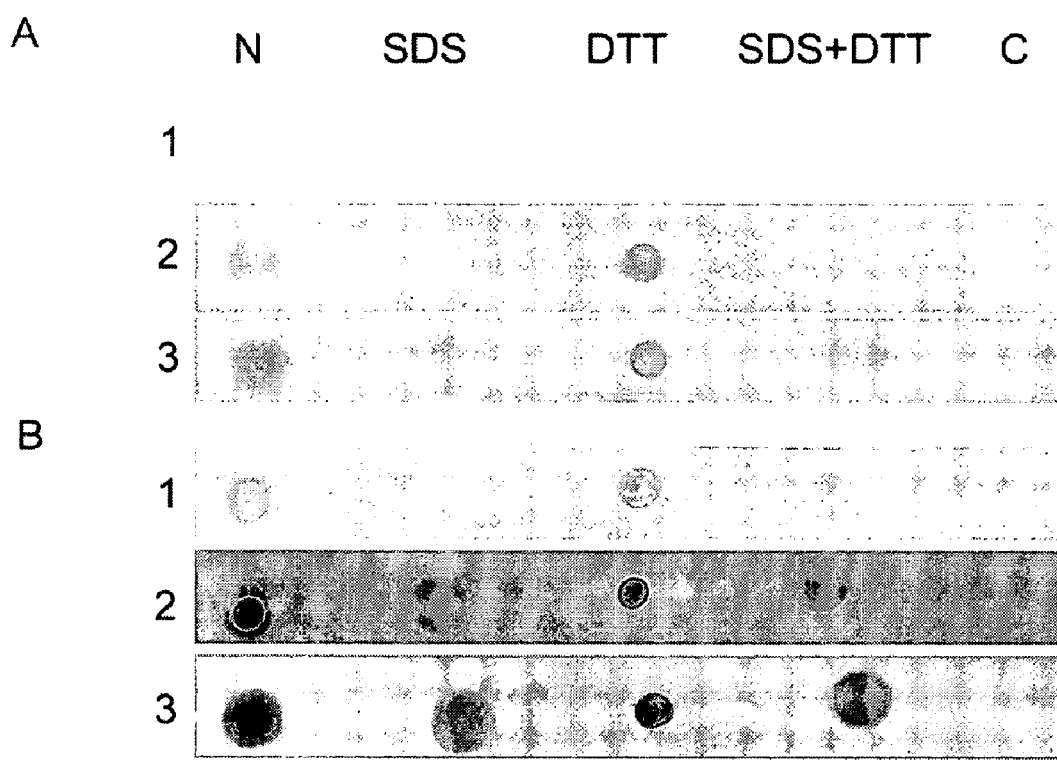
FIG. 2 shows a representative protein dot blot with recombinant Fbp from *E. canis* incubated under native conditions (N), denaturing conditions with 0.1% sodium dodecyl sulfate (SDS), reducing conditions with 50 mM of dithiothreitol (DTT), or in the presence of both SDS and DTT. Serum samples from *E. canis* infected dogs (1-3) collected on day 28 (A) and day 42 (B) post-inoculation. A recombinant protein expression control (C) with chloramphenicol acetyl transferase expressed by the same expression vector was used as a negative control.

The recombinant protein was recognized by serum from experimentally infected dogs, thereby confirming its immunogenicity. All dogs strongly recognized the protein primarily in a conformationally dependent manner. This is the likely reason that this protein is weakly reactive in native *E. canis* lysates (FIG. 1), yet was identified in a genomic library screened with antibody at a high dilution factor, and could explain the lack of immunoreactivity of the previously reported *E. chaffeensis* orthologous protein (Yu et al., 1999). The dependence on native conformation for strong antibody recognition by Fbp (FIG. 2) demonstrates that proteins not identified as immunoreactive by Western blot could potentially contain major immunoreactive epitopes. Conformational dependence of the Fbp illustrates the importance of identification of proteins with both linear and conformational epitopes and the limitations of Western blotting for comprehensive identification of all immunoreactive proteins that may be of interest for vaccine development.

Rickettsial genomes are believed to have been evolved from larger genomes (Andersson and Andersson, 1999). In the course of adaptation to an obligate intracellular lifestyle, certain genes become obsolete with the ability to utilize host resources. In the interest of minimizing energy expenditures for genome replication and transcription, these non-essential genes are mutated and subsequently deleted (Andersson and Andersson, 1999). This genome reduction process could explain the loss of the fbp operon system in *Ehrlichia*. The role for Fbp as a periplasmic iron transporter after extracellular competition with host proteins became unnecessary. However, the gene was conserved along with the ability of the protein to bind iron, suggesting that Fbp adapted to serve in a novel manner.

This invention concerns *Ehrlichia*Fbp does not remain in the periplasmic space as do other bacterial Fbps, but is found in the cytoplasm and on the surface as well. There have been reports of surface expression of Fbp in *Neisseria meningiditis* and bactericidal activity of antibodies against this protein (Gomez et al., 1996; Gomez et al., 1998). As *E. chaffeensis* was reported to be highly susceptible to an intracellular iron chelator (Barnewall et al., 1999), in specific embodiments of the invention this protein plays a critical role for the survival of the organism and presents compositions and methods related to vaccine development, such as subunit vaccine development.

Example 10

Exemplary Materials and Methods of the Present Invention

The present Example provides exemplary materials and methods for use in the present invention.

*Ehrlichia* and Purification. *E. canis* (Jake isolate) was propogated as previously described (McBride et al., 2001). *Ehrlichiae* were purified by size exclusion over Sephacryl S-1000 (Amersham Biosciences, Piscataway, N.J.) as previously described (Rikihisa et al., 1992). The initial fraction containing bacteria was frozen and utilized as an antigen source.

Identification of *E. canis* Fbp. Fbp was identified in an *E. canis* HpaII genomic library screened with anti-*E. canis* antiserum as previously described (McBride et al., 2001).

DNA Sequencing. Inserts were sequenced with an ABI Prism 377XL DNA Sequencer (Perkin-Elmer Applied Biosystems, Foster City, Calif.) at the University of Texas Medical Branch Protein Chemistry Core Laboratory using the forward and reverse primers (Uni 1) provided with the kit (Invitrogen, Carlsbad, Calif.).

PCR Amplification of the *Ehrlichia* spp. fbp Gene.

Regions of the *E. canis* fbp gene selected for PCR amplification were chosen by the Primer Select software (DNAstar, Madison, Wis.). Primers (400 nM) corresponding to nucleotides 82 to 101 (5'-CAA GAT CAG AAA CAA GAA GT, forward; SEQ ID NO:3) within the ORF and a region 198 bp downstream of the ORF (5'-TAA AAT AAA ATA GAA AGA AT, reverse; SEQ ID NO:4) were used to amplify the fbp gene. Template *E. canis* DNA (from the Jake isolate) was amplified using the PCR Master mix (F. Hoffmann-La Roche Ltd, Basel, Switzerland) with a thermal cycling profile of 95° C. for 4 min and 30 cycles of 95° C. for 30 s, 55° C. for 30 s, and 72° C. for 1 min, followed by a 72° C. extension for 7 min and a 4° C. hold. PCR products were analyzed in 1% agarose gels. Degenerate primers were designed (forward: 5'-ATG ATG AGA TTR MTT GCT TG (SEQ ID NO:5) where R=A or G and M=A or C; reverse: 5'-CTA TCT CCA MCC ACA CTC AT (SEQ ID NO:6) where M=A or C) for conserved regions in the coding regions of fbp from *E. canis* and *E. chaffeensis* corresponding to bp 1 through 20 (forward) and 1025 through 1044 (reverse). These primers were used to amplify the fbp gene in *E. muris* to compare sequence homology.

Signal Sequence Determination.

The *E. canis* Fbp was tested for the presence of a signal sequence with the computational algorithm SignalP trained on gram-negative bacteria (Nielsen et al., 1997).

Cloning and Expression of Recombinant *E. canis* Fbp.

The amplified PCR product was cloned directly into a universal TOPO TA Echo vector (pUni, Invitrogen). This vector was recombined with the acceptor vector pRSET, designed to produce proteins with a native C-terminus and an N-terminal polyhistidine region for purification. TOP10 *E. coli* (Invitrogen) were transformed with the plasmid containing the cloned fbp gene, and positive transformants were screened by PCR for the presence of the insert and correct orientation and sequenced to confirm the correct reading frame of the fbp gene. Expression of the recombinant Fbp was then performed in BL21(DE3)/pLysS *E. coli* (Invitrogen) after induction with 1.0 mM IPTG (isopropyl-beta-D-thiogalactopyranoside) for 3 h at 37° C. Bacteria were harvested by centrifugation at 5,000×g for 20 min and resuspended in phosphate-buffered saline. Recombinant Fbp was purified under native conditions by sonicating the pelleted bacteria resuspended in PBS (Braun-Sonic 2000) two times at 40 W for 30 s on ice. Recombinant Fbp was purified under native conditions after centrifugation at 10,000 ×g for 20 min to remove insoluble material. The clarified supernatant was loaded onto an equilibrated nickel-nitrilotriacetic acid (Ni-NTA) agarose column (Qiagen, Valencia, Calif.). The bound recombinant protein was washed with five column volumes of increasing concentrations 0.8, 8 mM, and 40 mM) of imidazole (Sigma-Aldrich, St. Louis, Mo.) and eluted with PBS plus 80 mM imidazole. Purified recombinant protein was dialyzed against PBS using Microcon centrifugal concentrators with a 30 kDa cutoff (Millipore, Billerica, Mass.).

Gel Electrophoresis and Immunoblotting.

Purified *E. canis* antigens were separated by SDS-PAGE and blotted for Western blots performed as previously described (McBride et al., 2003), except primary antibodies were diluted (1:500). Dot blot analyses were conducted with native protein, protein plus 0.1% w/v SDS, protein with 50 mM dithiothreitol (Invitrogen), or a combination of SDS plus reducing agent. Western analysis was performed as described above.

Rabbit Immunization.

A New Zealand White rabbit (Myrtle's Rabbitry Inc., Thompson Station, Tenn.) was immunized with the recombinant *E. canis* Fbp protein. Recombinant protein (100 µg) in 0.5 mL was mixed with an equal volume of Freund's complete adjuvant (Sigma) for the first injection and with Freund's incomplete adjuvant for the subsequent injections. The rabbit was immunized subcutaneously twice at 2 week intervals.

Analysis of Genomic Organization.

Genome sequences of *Ehrlichia canis* (see, for example, on the website of the Department of Energy Joint Genome Institute) and *E. chaffeensis* (see, for example, on the website of The Institute for Genome Research) were used to search for Ehrlichial genes involved in iron acquisition. Several kilobases of genome sequence flanking fbp were analyzed for neighboring ORFs using MapDraw software (DNAstar). The ORFs were identified with the basic local alignment search tool (BLAST) for related proteins. The fbp regions of *Wolbachia pipiens* (NCBI Accession number NC_002978), *Neorickettsia sennetsu* (TIGR_222891 contig 36), and *Anaplama marginale* (NCBI Accession AF305077) were located with BLAST and analyzed with MapDraw. The sequences fbpABC from *Neisseria gonorrhoeae* and yfeABCD from *Yersinia pestis* were from exemplary NCBI Accession numbers U33937 and U50597, respectively. Fur box identification was based on similarity to the consensus Fur recognition sequence N ATA/TAT (Escolar et al., 1999).

Reverse Transcriptase (RT)-PCR. RT-PCR was conducted on RNA extracted from *E. canis* infected DH82 cells and uninfected DH82 cells using the RNEasy kit (Qiagen). Contaminating DNA in the RNA preparation was removed with DNAse treatment (DNA-freeTM, Ambion, Austin, Tex.). Reactions were conducted with the Superscript IIITM One-step RT-PCR System with Platinum® DNA Polymerase (Invitrogen) in 50 µL total volume. Primers (400 nM) used to amplify fbp were the degenerate primers described above; membrane permease primers were 5'-AAT GGG CGT ATA GTA GGA GGA T (forward; SEQ ID NO:7) and 5'-TAA CGC AAT AAT AGA ACC AAG AAC (reverse; SEQ ID NO:8), corresponding to bp 25-46 and 514-537, respectively; primers to amplify the intergenic region were the 5'-ATG AGT GTG GKT GGA GAT AG (SEQ ID NO:9, forward (1025-1044 of fbp) and 5'-ACA ACA CAT AAT CAT ACC ATA CTA, reverse (SEQ ID NO:10) (104-127 of membrane permease). Template RNA (125 ng) was added to each reaction, and genomic *E. canis* DNA (350 ng) was added to the control reaction with RT-PCR reagent. The reactions were carried out with 30-min at 50° C. for the reverse transcription followed by 94° C. for 2 min and a thermal cycling profile of 10 cycles of 94° C. for 30 s, 50° C. for 30 s, and 68° C. for 1 min, followed by 25 cycles of 94° C. for 30 s, 50° C. for 30 s, and 68° C. for 1 min plus 5 sec for each additional cycle, and finished with a 72° C. extension for 7 min and a 4° C. hold. PCR products were analyzed in 1% agarose gels. The control reactions without reverse transcriptase were carried out with the Platinum PCR Supermix (Invitrogen) that had been demonstrated to amplify the products in the presence of genomic DNA (data not shown).

Structural Modeling. Modeling of the *E. canis* Fbp was conducted using Swiss-Model (see, for example, the website of SWISS-MODEL, which is a fully automated protein structure homology-modeling server, accessible via the ExPASy web server). *E. canis* Fbp was searched against known structures and modeled against the Fbp's from *Neisseria gonorrhoeae* (PDB 107T and 1D9Y), *Haemophilus influenzae* (PDB 1MRP and 1D9V), and *Mannheimia (Pasteurella)*

*haemolytica* (PDB 1Q35A). The results were visualized with Deep View (see, for example, the website of Deep View Swiss-PdbViewer via ExPASy). The *Neisseria gonhorrhoeae* Fbp structure from PDB 1O7T was used to generate the ribbon diagram in FIG. 3.

Iron Binding Determination. Following expression of recombinant *E. canis* Fbp, the *E. coli* bacterial pellet was resuspended in buffer containing 50 mM MES and 200 mM KCl (pH 6.8) and soluble extracts were purified over a Ni-NTA column as described above. The column was washed with 1× PBS and the matrix-bound protein turned red, indicative of iron binding. The protein was eluted from the column and the absorbance of the purified *E. canis* Fbp was evaluated by a spectral scan (240-700 nm; Perkin Elmer MBA2000 spectrophotometer, Wellesley, Mass.) to determine the absorbance wavelength indicative of iron binding. To compete off iron binding, the recombinant protein was incubated in an excess of sodium citrate or nitrilotriacetic acid to produce apo Fbp (iron free). In addition, purified recombinant Fbp was tested for iron binding with a Ferene S stain (Chung, 1985). The stain consisted of 0.75 mM Ferene S, 2% glacial acetic acid, and 15 mM thioglycolic acid. The recombinant protein was combined with the Ferene S stain, dot blotted onto a nitrocellulose membrane, and observed for a blue color.

Immunoelectron Microscopy. *E. canis* and *E. chaffeensis* infected cells were fixed in a mixture of 2.5% formaldehyde and 0.5% glutaraldehyde in 0.1 M cacodylate buffer (pH 7.2), postfixed in 1% OsO4 in 0.1 M cacodylate buffer, and stained en bloc with 1% uranyl acetate in 0.1 M maleate buffer, then dehydrated in ethanol and embedded in LR White (SPI Supplies, West Chester Penn.). Ultrathin sections were cut using a Reichert-Leica Ultracut S ultramicrotome and placed onto Formvar and carbon-coated nickel grids. Antigen grids were treated in blocking buffer with 0.1% bovine serum albumin (BSA) and 0.01 M glycerine in TBS for 15 minutes at room temperature and then incubated with rabbit anti-*E. canis* Fbp polyclonal antibody (diluted 1:1000 in diluting buffer, 0.05 M TBS with 1% BSA) for 1 hour at room temperature, then overnight at 4° C. The grids were washed in blocking buffer and incubated for 1 hour at room temperature with goat anti-rabbit IgG (H+L) labeled with 10 nm colloidal gold particles (AutoProbe EM goat anti-rabbit IgG G15, RPN422; Amersham Life Science, Piscataway, N.J.) diluted 1:20 in diluting buffer.

Nucleotide Sequence Accession Numbers. The fbp sequences of *Ehrlichia canis* and *E. muris* have been deposited into GenBank and assigned accession numbers. The exemplary *E. canis* sequence comprises the polynucleotide of AY520460 (SEQ ID NO:1), which encodes the polypeptide of AAS92975 (SEQ ID NO:2). The exemplary *E. muris* sequence comprises the polynucleotide of AY520461 (SEQ ID NO:13), which encodes the polypeptide of AAS92976 (SEQ ID NO:12). *E. chaffeensis* fbp is available in Genbank with accession number AF117273 (SEQ ID NO:13), which is a polynucleotide that encodes the polypeptide of AAD32554 (SEQ ID NO:14).

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference herein.

PUBLICATIONS

Adhikari, P., S. A. Berish, A. J. Nowalk, K. L. Veraldi, S. A. Morse, and T. A. Mietzner. 1996. The fbpABC locus of *Neisseria gonorrhoeae* functions in the periplasm-to-cytosol transport of iron. J.Bacteriol. 178:2145-2149.

Adhikari, P., S. D. Kirby, A. J. Nowalk, K. L. Veraldi, A. B. Schryvers, and T. A. Mietzner. 1995. Biochemical characterization of a *Haemophilus influenzae* periplasmic iron transport operon. J.Biol.Chem. 270:25142-25149.

Altuvia, S., M. Almiron, G. Huisman, R. Kolter, and G. Storz. 1994. The dps promoter is activated by OxyR during growth and by IHF and sigma S in stationary phase. Mol.Microbiol. 13:265-272.

Andersson, J. O. and S. G. Andersson. 1999. Insights into the evolutionary process of genome degradation. Curr.Opin. Genet.Dev. 9:664-671.

Andrews, S. C., A. K. Robinson, and F. Rodriguez-Quinones. 2003. Bacterial iron homeostasis. FEMS Microbiol.Rev. 27:215-237.

Angerer, A., S. Gaisser, and V. Braun. 1990. Nucleotide sequences of the sfuA, sfuB, and sfuC genes of *Serratia marcescens* suggest a periplasmic-binding-protein-dependent iron transport mechanism. J.Bacteriol. 172:572-578.

Barnewall, R. E., N. Ohashi, and Y. Rikihisa. 1999. *Ehrlichia chaffeensis* and *E. sennetsu*, but not the human granulocytic ehrlichiosis agent, colocalize with transferrin receptor and up-regulate transferrin receptor mRNA by activating iron-responsive protein 1. Infect.Immun. 67:2258-2265.

Barnewall, R. E., Y. Rikihisa, and E. H. Lee. 1997. *Ehrlichia chaffeensis* inclusions are early endosomes which selectively accumulate transferrin receptor. Infection & Immunity 65:1455-1461.

Bearden, S. W. and R. D. Perry. 1999. The Yfe system of *Yersinia pestis* transports iron and manganese and is required for full virulence of plague. Mol.Microbiol. 32:403-414.

Bearden, S. W., T. M. Staggs, and R. D. Perry. 1998. An ABC transporter system of *Yersinia pestis* allows utilization of chelated iron by *Escherichia coli* SAB 11. J.Bacteriol. 180:1135-1147.

Bruns, C. M., A. J. Nowalk, A. S. Arvai, M. A. McTigue, K. G. Vaughan, T. A. Mietzner, and D. E. McRee. 1997. Structure of *Haemophilus influenzae* Fe(+3)-binding protein reveals convergent evolution within a superfamily. Nat.Struct-.Biol. 4:919-924.

Bruns, C. M., D. S. Anderson, K. G. Vaughan, P. A. Williams, A. J. Nowalk, D. E. McRee, and T. A. Mietzner. 2001. Crystallographic and biochemical analyses of the metal-free *Haemophilus influenzae* Fe3+-binding protein. Biochemistry 40:15631-15637.

Chung, M. C. 1985. A specific iron stain for iron-binding proteins in polyacrylamide gels: application to transferrin and lactoferrin. Anal.Biochem. 148:498-502.

Clarke, T. E., L. W. Tari, and H. J. Vogel. 2001. Structural biology of bacterial iron uptake systems. Curr.Top.Med. Chem. 1:7-30.

Desai, P. J., A. Angerer, and C. A. Genco. 1996. Analysis of Fur binding to operator sequences within the *Neisseria gonorrhoeae* fbpA promoter. J.Bacteriol. 178:5020-5023.

Escolar, L., J. Perez-Martin, and L. de, V. 1999. Opening the iron box: transcriptional metalloregulation by the Fur protein. J.Bacteriol. 181:6223-6229.

Frazier, B. A., J. D. Pfeifer, D. G. Russell, P. Falk, A. N. Olsen, M. Hammar, T. U. Westblom, and S. J. Normark. 1993. Paracrystalline inclusions of a novel ferritin containing nonheme iron, produced by the human gastric pathogen *Helicobacter pylori*: evidence for a third class of ferritins. J.Bacteriol. 175:966-972.

Gomez, J. A., C. Agra, L. Ferron, N. Powell, M. Pintor, M. T. Criado, and C. M. Ferreiros. 1996. Antigenicity, cross-reactivity and surface exposure of the *Neisseria meningitidis* 37 kDa protein (Fbp). Vaccine 14:1340-1346.

Gomez, J. A., M. T. Criado, and C. M. Ferreiros. 1998. Bactericidal activity of antibodies elicited against the *Neisseria meningitidis* 37-kDa ferric binding protein (FbpA) with different adjuvants. FEMS Immunol.Med.Microbiol. 20:79-86.

Ishikawa, T., Y. Mizunoe, S. Kawabata, A. Takade, M. Harada, S. N. Wai, and S. Yoshida. 2003. The iron-binding protein Dps confers hydrogen peroxide stress resistance to *Campylobacter jejuni*. J.Bacteriol. 185:1010-1017.

Janakiraman, A. and J. M. Slauch. 2000. The putative iron transport system SitABCD encoded on SPI1 is required for full virulence of *Salmonella typhimurium*. Mol.Microbiol. 35:1146-1155.

Kirby, S. D., F. A. Lainson, W. Donachie, A. Okabe, M. Tokuda, O. Hatase, and A. B. Schryvers. 1998. The *Pasteurella haemolytica* 35 kDa iron-regulated protein is an FbpA homologue. Microbiology 144 (Pt 12):3425-3436.

McBride J W, R. E. Corstvet, S. D. Gaunt, C. Boudreaux, T. Guedry, and D. H. Walker. 2003. Kinetics of antibody response to *Ehrlichia canis* immunoreactive proteins. Infect.Immun. 71:2516-2524.

McBride, J. W., R. E. Corstvet, E. B. Breitschwerdt, and D. H. Walker. 2001. Immunodiagnosis of *Ehrlichia canis* infection with recombinant proteins. J.Clin.Microbiol. 39:315-322.

Mietzner, T. A., S. B. Tencza, P. Adhikari, K. G. Vaughan, and A. J. Nowalk. 1998. Fe(III) periplasm-to-cytosol transporters of gram-negative pathogens. Curr.Top.Microbiol.Immunol. 225:113-135.

Nielsen, H., J. Engelbrecht, S. Brunak, and G. von Heijne. 1997. Identification of prokaryotic and eukaryotic signal peptides and prediction of their cleavage sites. Protein Eng 10:1-6.

Nowalk, A. J., S. B. Tencza, and T. A. Mietzner. 1994. Coordination of iron by the ferric iron-binding protein of pathogenic *Neisseria* is homologous to the transferring. Biochemistry 33:12769-12775.

Popov, V. L., S. M. Chen, H. M. Feng, and D. H. Walker. 1995. Ultrastructural variation of cultured *Ehrlichia chaffeensis*. Journal of Medical Microbiology 43:411-421.

Raymond, K. N., E. A. Dertz, and S. S. Kim. 2003. Enterobactin: an archetype for microbial iron transport. Proc.Natl.Acad.Sci.U.S.A 100:3584-3588.

Rikihisa, Y., S. A. Ewing, J. C. Fox, A. G. Siregar, F. H. Pasaribu, and M. B. Malole. 1992. Analyses of *Ehrlichia canis* and a canine granulocytic *Ehrlichia* infection. J.Clin.Microbiol. 30:143-148.

Romao, C. V., M. Regalla, A. V. Xavier, M. Teixeira, M. Y. Liu, and J. Le Gall. 2000. A bacterioferritin from the strict anaerobe *Desulfovibrio desulfuricans* ATCC 27774. Biochemistry 39:6841-684.

Sebastian, S. and C. A. Genco. 1999. FbpC is not essential for iron acquisition in *Neisseria gonorrhoeae*. Infect.Immun. 67:3141-3145.

Shouldice, S. R., D. R. Dougan, P. A. Williams, R. J. Skene, G. Snell, D. Scheibe, S. Kirby, D. J. Hosfield, D. E. McRee, A. B. Schryvers, and L. W. Tari. 2003. Crystal structure of *Pasteurella haemolytica* ferric ion-binding protein A reveals a novel class of bacterial iron-binding proteins. J.Biol.Chem. 278:41093-41098.

Shouldice, S. R., D. R. Dougan, R. J. Skene, L. W. Tari, D. E. McRee, R. H. Yu, and A. B. Schryvers. 2003. High resolution structure of an alternate form of the ferric ion binding protein from *Haemophilus influenzae*. J.Biol.Chem. 278: 11513-11519.

Touati, D., M. Jacques, B. Tardat, L. Bouchard, and S. Despied. 1995. Lethal oxidative damage and mutagenesis are generated by iron in delta fur mutants of *Escherichia coli*: protective role of superoxide dismutase. J.Bacteriol. 177:2305-2314.

Yariv, J., A. J. Kalb, R. Sperling, E. R. Bauminger, S. G. Cohen, and S. Ofer. 1981. The composition and the structure of bacterioferritin of *Escherichia coli*. Biochem.J. 197:171-175.

Yu, X. J., P. A. Crocquet-Valdes, L. C. Cullman, V. L. Popov, and D. H. Walker. 1999. Comparison of *Ehrlichia chaffeensis* recombinant proteins for serologic diagnosis of human monocytotropic ehrlichiosis. J.Clin.Microbiol. 37:2568-2575.

Zhao, G., P. Ceci, A. Ilari, L. Giangiacomo, T. M. Laue, E. Chiancone, and N. D. Chasteen. 2002. Iron and hydrogen peroxide detoxification properties of DNA-binding protein from starved cells. A ferritin-like DNA-binding protein of *Escherichia coli*. J.Biol.Chem. 277:27689-27696.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An isolated polynucleotide, comprising:
   a) SEQ ID NO:2; or
   b) a polynucleotide that is at least about 95% identical to SEQ ID NO:2.

2. The polypeptide of claim 1, comprised in a pharmaceutically acceptable excipient.

3. The polypeptide of claim 1, comprised in a pharmaceutical composition suitable as an immunogenic composition.

4. A method of inducing an immune response in an individual, comprising the step of administering to the individual a therapeutically effective amount of the polypeptide of claim 1, wherein said administering induces the immune response.

5. The polypeptide of claim 1, wherein the polypeptide of b) is a polypeptide that is at least 97% identical to SEQ ID NO:2.

6. The polypeptide of claim 1, wherein the polypeptide of b) is a polypeptide that is at least 99% identical to SEQ ID NO:2.

* * * * *

SEQUENCE LISTING

<160> NUMBER OF SEQ ID NOS: 16

<210> SEQ ID NO 1
<211> LENGTH: 1044

```
<212> TYPE: DNA
<213> ORGANISM: Ehrlichia canis

<400> SEQUENCE: 1
atgatgagat tgcttgcttg ccttggtatt gtagctgtta ttattgtggc ttttaatttt     60
ttaactaata acaacaag

```
Asp Lys Ile Leu Val Arg Ser Ser Ser Pro Tyr Asn Gln Ser Leu
                165                 170                 175

Ile Ala Phe Met Val Ala Asn Asn Gly Val Glu Asn Thr Lys Ile Trp
            180                 185                 190

Val Lys Gly Leu Val Ala Asn Met Ala Arg Lys Pro Ser Gly Gly Asp
        195                 200                 205

Ile Asp Gln Ile Tyr Ala Val Ala Ala Asp Glu Gly Ser Ile Ala Ile
    210                 215                 220

Val Asn Ser Tyr Tyr Phe Gly Arg Ile Ala Ala Ser Asp Lys Lys Ser
225                 230                 235                 240

Asp Gln Ala Val Val Lys Lys Leu Gly Ile Phe Phe Pro Asn Gln Glu
                245                 250                 255

Thr Thr Gly Thr Met Ile Asn Ile Ser Gly Gly Ala Val Thr Lys His
            260                 265                 270

Ala Lys Asn Lys Gln Asn Ala Ile Lys Leu Leu Glu Phe Leu Thr Ser
        275                 280                 285

Val Arg Ala Gln Lys Val Tyr Ala Gln Val Asn Gln Glu Tyr Pro Ile
    290                 295                 300

Val Glu Gly Val Glu Leu Ser Glu Val Leu Lys Thr Phe Gly Thr Phe
305                 310                 315                 320

Lys Glu Ser Asp Leu Pro Leu Gln Glu Leu Glu Lys His Leu Thr Lys
                325                 330                 335

Ser Val Glu Ile Ala Asp Glu Cys Gly Trp Arg
            340                 345

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
caagatcaga aacaagaagt                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 4
taaaataaaa tagaaagaat                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: modified_base
<222> LOCATION: (12)
<223> OTHER INFORMATION: R = A or G
<220> FEATURE:
<221> NAME/KEY: modified_base
<222> LOCATION: (13)
<223> OTHER INFORMATION: M = A or C
```

```
<400> SEQUENCE: 5
atgatgagat trmttgcttg                                               20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: modified_base
<222> LOCATION: (10)
<223> OTHER INFORMATION: M = A or C

<400> SEQUENCE: 6
ctatctccam ccacactcat                                               20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
aatgggcgta tagtaggagg at                                            22

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
taacgcaata atagaaccaa gaac                                          24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
atgagtgtgg ktggagatag                                               20

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
acaacacata atcataccat acta                                          24

<210> SEQ ID NO 11
<211> LENGTH: 1044
<212> TYPE: DNA
<213> ORGANISM: Ehrlichia muris
```

<400> SEQUENCE: 11

```
atgatgagat tgattgcttg ttttagtatc attgctgtta ttatgttagc ttttaatttc      60
tttactaaaa gacaacaagt tcaaaattca ggacaagagg tacgcgtgta ttcatctcgt     120
aaggaagaat tgttacatag tttgtttgag caatttacta agaaactgg tataaatgtt      180
cagtatatta atgatgaagc tgctcaactt attaatagaa tggaaaatga aggtactgct     240
acttcagctg atgtattttt gactgcagat gctgttaatc ttattcttgc taagaaaaat    300
ggattattac agcctgtgca atctgaagta ctaaatcaag caattcctag caagtataga    360
gatagtgatg gattttggtt tggattgacg aagcgtgcaa gggtgatagt atataacaag    420
gatgtaattg aagagagtga gttgagtaca tatgagtacc ttgcaaatac gaaatggaaa    480
gataaaattt aataagatc ttctagtagc ccatataatc agtcgttaat tgcttttatg    540
atagcaaata atggtataga gaatactaag atttggatta aaggtttagt ttcgaatatg    600
gctaggaaac ctagcggtgg agatatagat caaatttatg ctgttgcagc agatgaaggt    660
agtatcgcta tagttaatag ttattatttt gggagaattg cagcttctaa caaaaaagt    720
gatcaagctg cagttaaaaa acttggtatc ttttttccta atcaggaaac tactggtact    780
atgattaata ttagtggcgg tgctgttaca aaacatgcaa gaacaagca aaatgctata     840
aggttgttgg agttttttggc cagtgtaaag gcacagaggg tttatgctca agttaatcaa    900
gagtatcctg ttgtagaagg ggtagagatt tcagacgttt tgaaaactt tggtgtattt    960
aaagagagta atttaccttt acaggaacta gaggagcatt taactgaatc tgttaaaatt   1020
gcagatgagt gtggttggag atag                                          1044
```

<210> SEQ ID NO 12
<211> LENGTH: 347
<212> TYPE: PRT
<213> ORGANISM: Ehrlichia muris

<400> SEQUENCE: 12

```
Met Met Arg Leu Ile Ala Cys Phe Ser Ile Ile Ala Val Ile Met Leu
  1               5                  10                  15

Ala Phe Asn Phe Phe Thr Lys Arg Gln Gln Val Gln Asn Ser Gly Gln
             20                  25                  30

Glu Val Arg Val Tyr Ser Ser Arg Lys Glu Glu Leu Leu His Ser Leu
         35                  40                  45

Phe Glu Gln Phe Thr Lys Glu Thr Gly Ile Asn Val Gln Tyr Ile Asn
     50                  55                  60

Asp Glu Ala Ala Gln Leu Ile Asn Arg Met Glu Asn Glu Gly Thr Ala
 65                  70                  75                  80

Thr Ser Ala Asp Val Phe Leu Thr Ala Asp Ala Val Asn Leu Ile Leu
                 85                  90                  95

Ala Lys Lys Asn Gly Leu Leu Gln Pro Val Gln Ser Glu Val Leu Asn
            100                 105                 110

Gln Ala Ile Pro Ser Lys Tyr Arg Asp Ser Asp Gly Phe Trp Phe Gly
        115                 120                 125

Leu Thr Lys Arg Ala Arg Val Ile Val Tyr Asn Lys Asp Val Ile Glu
    130                 135                 140

Glu Ser Glu Leu Ser Thr Tyr Glu Tyr Leu Ala Asn Thr Lys Trp Lys
145                 150                 155                 160

Asp Lys Ile Leu Ile Arg Ser Ser Ser Pro Tyr Asn Gln Ser Leu
                165                 170                 175
```

-continued

```
Ile Ala Phe Met Ile Ala Asn Asn Gly Ile Glu Asn Thr Lys Ile Trp
            180                 185                 190
Ile Lys Gly Leu Val Ser Asn Met Ala Arg Lys Pro Ser Gly Gly Asp
        195                 200                 205
Ile Asp Gln Ile Tyr Ala Val Ala Ala Asp Glu Gly Ser Ile Ala Ile
    210                 215                 220
Val Asn Ser Tyr Tyr Phe Gly Arg Ile Ala Ala Ser Asn Lys Lys Ser
225                 230                 235                 240
Asp Gln Ala Ala Val Lys Lys Leu Gly Ile Phe Phe Pro Asn Gln Glu
                245                 250                 255
Thr Thr Gly Thr Met Ile Asn Ile Ser Gly Gly Ala Val Thr Lys His
            260                 265                 270
Ala Lys Asn Lys Gln Asn Ala Ile Arg Leu Leu Glu Phe Leu Ala Ser
        275                 280                 285
Val Lys Ala Gln Arg Val Tyr Ala Gln Val Asn Gln Glu Tyr Pro Val
    290                 295                 300
Val Glu Gly Val Glu Ile Ser Asp Val Leu Lys Thr Phe Gly Val Phe
305                 310                 315                 320

Lys Glu Ser Asn Leu Pro Leu Gln Glu Leu Glu Glu His Leu Thr Glu
                325                 330                 335
Ser Val Lys Ile Ala Asp Glu Cys Gly Trp Arg
            340                 345

<210> SEQ ID NO 13
<211> LENGTH: 4735
<212> TYPE: DNA
<213> ORGANISM: Ehrlichia chaffeensis
<220> FEATURE:
<221> NAME/KEY: modified_base
<222> LOCATION: (2447)
<223> OTHER INFORMATION: n = a, c, g, and/or t/u

<400> SEQUENCE: 13
ttccctctct taataattat taaatatttt atataattat tacttaatta taatttttat      60
gttgtaaaaa acattaatta ataaattcat taatattttt agataaaaat gtcaatatat     120
tatatctaaa aagcaatcaa taagttaatt tattaacttt tttatattga cattttaaca     180
tatcttgtgt atgataccga tctaaattaa tatttattaa caaatgaatt atatgacagt     240
ttttttcgaa tataatggca gtaaagttaa cactaaggaa gtagtgaaac gcaatactgc     300
aggtagaaca gatcaagata aggactcttc tacctatgta tataatactt ataacgctgg     360
tgatctacaa gggcatgtac aacagtcctt tatgagaaat aatgctgagc acaatagaac     420
agatactgtt cttccttata atgatagtta tggctctacc tgttgtgcct gctgtagaaa     480
ctggtgctga tggtaattca ggtaagggta attctgtaga ttttaaatct aatgtttttt     540
gtaatacgca tactataaga gacgatcagt tgaaattaaa tctagaaata cacactttag     600
gaaatttatc tgatagaaga ttacaggaga ttaagaaagg atttgatgat tcaataataa     660
gatttaaaga taattttggg ttggaaccca atgaaaaaga tactactttt gaattatatc     720
tttttgatga taaagaacaa tatgagcatt atggacggct ttataatcta ggaataaatg     780
gagctggtgg tatgactttt tatggagatg ctgatgttcc ttataaaatt tatgtatatc     840
agtttggtga aatattaaat ttaaaacatg agttaactca tgctttagag aattatgcgt     900
ctggacactc attgtctaag cttaaaataa atcatgatat atttacagaa gggttggctg     960
actatataca aaatgatggt acttttatta tgagagaatt aagagataaa gaagtaacat    1020
```

```
caagtgtatt gaaggagggt tcttctaaag atatagatca agtcagtgat gctgcagtag    1080
ctaaggatca gcatttgagt tatagtatag acacgcatt tgtaacattt ttacaggaga     1140
attatcctgg tgtgatttca gagtactttg cagcattgag ggaaggtaat gctgtgcatg    1200
ctagagaaat aattagcatg aataagtatg cagatttga accgtgggta cagtctaaag     1260
acatttcttt gtatctagaa ggcatgaatg tattaaagat agatttagga gaaaaaatgt    1320
tttctgctaa aaacgctgtt tcttttgaaa ataagaatgt aagaaatgaa tattactgtg    1380
aaaacatttg tactatgaac ggtgaagtag tagggaaaat atctcctgtg gtgcattatg    1440
ccgataagga tactattcgt acttggaata ttgcgagtac tgatatgata gaagtaaaac    1500
cagagtatag ttttctaaaa ttggttagta ctccatctgg taagtctgca tatgtatatt    1560
gtgataagga tggtaatgag tattttaata ctcaatctta tgtggaatat gcgtttaata    1620
tcttgaaaaa atatgatgag aatcttcgta tcaatggtga ttttttagat attagaggtc    1680
gttactcaga tgctgataaa gtgtttgata aaattcctaa cgcagatttg ttgttggatc    1740
agttcttaga taaaattggt tatggaaatt ataagcaagt aataatgagc gacccagagc    1800
aggttagtgt tataaaaatg catatagtaa aaaaagcttt tgaagatttt agagaatctg    1860
aagtcaaaaa agtgtttact ggtgaatcag gtgttgattc tacaataaaa aatctattga    1920
tggatttaac ttatattaat ttaagtgatg tgataggagt aaatggttct aatattgaaa    1980
gcattgtatc tgatccaaat gtaatgttgc gtactgctat attaggtaag ggagatgcaa    2040
gtggaatctc tctgtatgta ggtgatcaaa aagtcgctga attatctact gaaggaggtt    2100
attgtgtgaa ggatcttgat actaataatg tgaattttgt attccgcaat gctgttggaa    2160
acatagcaag tagttatcaa gatagagcat acatggttgt atgtgaaaaa tatggtgaat    2220
ttactactgc tctaattgat gatatacaaa agacagagca tggaaatgtt atatgggata    2280
atcagtttaa tcatcctggt gttaatcatt tatatccaaa ttatcaaaag gtattattaa    2340
atgatgcttc acttaaggat tattcccatc ttgctaatac aaggtttcat catgatgata    2400
cagtaattgt acggggagat ctgttggatg acaaaggaac tgttacnacg agtgatgaca    2460
ttcatcaagc agtgattaaa catgatgatc aagtactaca tcaatttaaa agtatttctt    2520
tttacataag tgagccatca acaaataatg ctggaactta tggtagtgat ttctttattg    2580
ctgatgaagg gaaaaatctt agatttcaac ttcctaaaac aattactcat ttaaagttag    2640
taaatgttga tgggaatcaa aaattagtac catgtactgc agatggtaat gagcaccctg    2700
atggtatgcc atctaattta acagatgagt atcgatatat tgatcctatt tttgctcaca    2760
catttgagaa acaaagctat tctaaaaata gtgttagcat tggtttggta gattttgata    2820
aatatcaaga aggaactatg tttaaattac agtattattc tgatgattat catattaata    2880
aggatgaaca tggtaatata attagaccta ataatgtgtc tttaaaaaca aaagttgacc    2940
tggtatatga tgataaagtt atgggaatgt tatctgataa tgtaaataaa tttcagggag    3000 atgttttgt tgctgcaagc cttaattata gccacagtga ttttctttcg tctaaatatt    3060
ttcagaaggt caatattgaa gcgttagaaa atggggtata tagtggaaga tatgatgtag    3120
gaagtggtga tgaaatagcc aatcttgata ctgatgtagg ttatagtgac aaaactgttt    3180
tttattttaa aggaagtaat tcacctgttg atgtattaga taatgttgat actgtgtcta    3240
ctatttcacc ttatattaat gagtttcaat agattttaaa aaagaagcag cgttcaatga    3300
atgctgcttt cttgtatgtg tagagtcatt tttccgtgtg tatatttcac tataaatgaa    3360
ttttatatga cgttgtgaat aattctacga ttttacattg catgtatagt tttggtagat    3420
```

```
taaaaaagta gtgttttata tagattatga aaacgttttt taatgtatat ttggttattt    3480
tcatagtgtt ttatatgaat attttttatac gttttttaatt tatgaaaagt atatttataa  3540
ttataagtgt gctttaaagt agttctataa ttatatcaat attgcattta ttctgttgtc    3600
ttgtataata gtagggtttt gaatatttat ggattaaaac gatatgatga gattaattgc    3660
ttgtcttggt attatagctg ttgttatcct agcctttagt tttttttacta aaaagcagca   3720 cgttcaagat ttaacacaag aagtacgagt atattcatct cgcaaggaag aattattaca    3780
tagtttgttt aaacaattta ctaaagaaac tggtataaat gttaaataca tcaatgacga    3840
agccgctcaa cttattaata gaatggaaaa tgagggtact gctacttcag ctgatgtatt    3900
tttaactgca gatgctgtta atcttattct tgctaaaaag aaaggattgt tgcaacctgt    3960
tcaatctgaa gtgttgaatc aagcaattcc tagtaagtat agagatagtg aggggttttg    4020
gtttgggtta actaagcgtg caagggtgat agtatataac aaagatttag ttgaaaagag    4080
tgacttaagt acatatgagc accttgcaaa tacaaaatgg aaagataaaa ttttagtaag    4140
atcttctagc agtccatata accagtcttt aattgctttt atgatagcaa ataatggtat    4200
agaaaatact aagatttggg ttaaaggttt agtttcaaat atggctagga agcctagtgg    4260
tggggatata gatcaaattt atgctgttgc agcagatgaa ggtagtatag ctatagttaa    4320
tagttattat tttggtagga ttgcagcttc tgataagaag agtgatcaga ttgcagttaa    4380
aaaacttggt atcttttttcc ctaatcagga aaccacaggt actatgatta acattagtgg   4440
tggtgctgta acaaagaatg caaagaataa gcagaatgct ataagattgt tagagttttt    4500
aactagcgtg aaagcacaaa aggtctatgc tcaagttaat caagaatatc ctgttgtaga    4560
aggggtagag ctctcagaga ttttagggac ttttggttca tttaaggaga gcaatttgcc    4620
tttacaagaa ttagagaaac atttgactga agctgttaaa atggcagatg agtgtgggtg    4680
gagatagttt ttgaataaat tgaattctgt atataagttt acttcttaag tctaa         4735

<210> SEQ ID NO 14
<211> LENGTH: 347
<212> TYPE: PRT
<213> ORGANISM: Ehrlichia chaffeensis

<400> SEQUENCE: 14

Met Met Arg Le

```
Lys Ser Asp Leu Ser Thr Tyr Glu His Leu Ala Asn Thr Lys Trp Lys
145                 150                 155                 160

Asp Lys Ile Leu Val Arg Ser Ser Ser Pro Tyr Asn Gln Ser Leu
            165                 170                 175

Ile Ala Phe Met Ile Ala Asn Asn Gly Ile Glu Asn Thr Lys Ile Trp
            180                 185                 190

Val Lys Gly Leu Val Ser Asn Met Ala Arg Lys Pro Ser Gly Gly Asp
        195                 200                 205

Ile Asp Gln Ile Tyr Ala Val Ala Ala Asp Glu Gly Ser Ile Ala Ile
        210                 215                 220

Val Asn Ser Tyr Tyr Phe Gly Arg Ile Ala Ala Ser Asp Lys Lys Ser
225                 230                 235                 240

Asp Gln Ile Ala Val Lys Lys Leu Gly Ile Phe Phe Pro Asn Gln Glu
            245                 250                 255

Thr Thr Gly Thr Met Ile Asn Ile Ser Gly Gly Ala Val Thr Lys Asn
            260                 265                 270

Ala Lys Asn Lys Gln Asn Ala Ile Arg Leu Leu Glu Phe Leu Thr Ser
        275                 280                 285

Val Lys Ala Gln Lys Val Tyr Ala Gln Val Asn Gln Glu Tyr Pro Val
        290                 295                 300

Val Glu Gly Val Glu Leu Ser Glu Ile Leu Gly Thr Phe Gly Ser Phe
305                 310                 315                 320

Lys Glu Ser Asn Leu Pro Leu Gln Glu Leu Lys His Leu Thr Glu
            325                 330                 335

Ala Val Lys Met Ala Asp Glu Cys Gly Trp Arg
            340                 345

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
tattatttaa tgtaattatg                                              20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
aattattttg gaaaaataag                                              20
```